US010463673B2

(12) United States Patent
Cooper et al.

(10) Patent No.: US 10,463,673 B2
(45) Date of Patent: Nov. 5, 2019

(54) NANOPARTICULATE MELOXICAM FORMULATIONS

(71) Applicant: Recro Pharma, Inc., Malvern, PA (US)

(72) Inventors: Eugene R. Cooper, Berwyn, PA (US); Tuula Ryde, Malvern, PA (US); John Pruitt, Suwanee, GA (US); Laura Kline, Harleysville, PA (US)

(73) Assignee: Recro Pharma, Inc., Malvern, PA (US)

( * ) Notice: Subject to any disclaimer, the term of this patent is extended or adjusted under 35 U.S.C. 154(b) by 0 days.

(21) Appl. No.: 15/950,367

(22) Filed: Apr. 11, 2018

(65) Prior Publication Data

US 2018/0228809 A1 Aug. 16, 2018

Related U.S. Application Data

(63) Continuation of application No. 15/437,534, filed on Feb. 21, 2017, which is a continuation of application No. 13/941,076, filed on Jul. 12, 2013, now abandoned, which is a continuation of application No. 12/788,203, filed on May 26, 2010, now abandoned, which is a continuation-in-part of application No. 10/784,900, filed on Feb. 24, 2004, now Pat. No. 8,512,727.

(60) Provisional application No. 60/450,705, filed on Mar. 3, 2003.

(51) Int. Cl.
| | |
|---|---|
| A61K 9/14 | (2006.01) |
| A61K 31/5415 | (2006.01) |
| A61K 9/00 | (2006.01) |
| A61K 9/51 | (2006.01) |
| A61K 9/10 | (2006.01) |

(52) U.S. Cl.
CPC ........ *A61K 31/5415* (2013.01); *A61K 9/0019* (2013.01); *A61K 9/0053* (2013.01); *A61K 9/10* (2013.01); *A61K 9/14* (2013.01); *A61K 9/145* (2013.01); *A61K 9/146* (2013.01); *A61K 9/5123* (2013.01); *A61K 9/5138* (2013.01); *A61K 9/5169* (2013.01); *A61K 9/5192* (2013.01)

(58) Field of Classification Search
None
See application file for complete search history.

(56) References Cited

U.S. PATENT DOCUMENTS

| | | | |
|---|---|---|---|
| 4,233,299 | A | 11/1980 | Trummlitz et al. |
| 4,783,484 | A | 11/1988 | Violante et al. |
| 4,826,689 | A | 5/1989 | Violanto et al. |
| 4,997,454 | A | 3/1991 | Violante et al. |
| 5,133,908 | A | 7/1992 | Stainmesse et al. |
| 5,145,684 | A | 9/1992 | Liversidge et al. |
| 5,192,535 | A | 3/1993 | Davis et al. |
| 5,298,262 | A | 3/1994 | Na et al. |
| 5,302,401 | A | 4/1994 | Liversidge et al. |
| 5,318,767 | A | 6/1994 | Liversidge et al. |
| 5,326,552 | A | 7/1994 | Na et al. |
| 5,328,404 | A | 7/1994 | Bacon |
| 5,336,507 | A | 8/1994 | Na et al. |
| 5,340,564 | A | 8/1994 | Illig et al. |
| 5,346,702 | A | 9/1994 | Na et al. |
| 5,349,957 | A | 9/1994 | Yudelson |
| 5,352,459 | A | 10/1994 | Hollister et al. |
| 5,384,124 | A | 1/1995 | Courteille et al. |
| 5,399,363 | A | 3/1995 | Liversidge et al. |
| 5,401,492 | A | 3/1995 | Kellar et al. |
| 5,429,824 | A | 7/1995 | June |
| 5,447,710 | A | 9/1995 | Na et al. |
| 5,451,393 | A | 9/1995 | Liversidge et al. |
| 5,466,440 | A | 11/1995 | Ruddy et al. |
| 5,470,583 | A | 11/1995 | Na et al. |
| 5,472,683 | A | 12/1995 | Illig |
| 5,494,683 | A | 2/1996 | Liversidge et al. |
| 5,500,204 | A | 3/1996 | Osifo |
| 5,510,118 | A | 4/1996 | Bosch et al. |
| 5,518,187 | A | 5/1996 | Bruno et al. |
| 5,518,738 | A | 5/1996 | Eickhoff et al. |
| 5,521,218 | A | 5/1996 | Osifo |
| 5,525,328 | A | 6/1996 | Bacon et al. |
| 5,534,270 | A | 7/1996 | De Castro |
| 5,543,133 | A | 8/1996 | Swanson et al. |
| 5,552,160 | A | 9/1996 | Liversidge et al. |
| 5,560,931 | A | 10/1996 | Eickhoff et al. |
| 5,560,932 | A | 10/1996 | Bagchi et al. |
| 5,565,188 | A | 10/1996 | Wong et al. |
| 5,568,188 | A | 10/1996 | Wong et al. |
| 5,569,448 | A | 10/1996 | Wong et al. |
| 5,571,536 | A | 11/1996 | Eickhoff et al. |

(Continued)

FOREIGN PATENT DOCUMENTS

| | | |
|---|---|---|
| CA | 2326517 A1 | 10/1999 |
| DE | 2756113 | 6/1979 |

(Continued)

OTHER PUBLICATIONS

Narjes et al. "Pharmacokinetics and tolerability of meloxicam after i.m. administration", Br J Clin Pharmacol 1996; 41:135-139 (Year: 1996).*

Rao et al., "Evolution of Nonsteroidal Anti-Inflammatory Drugs (NSAIDs): Cyclooxygenase (COX) Inhibition and Beyond", J Pharm Pharmaceuit, 2008, pp. 81-110.

Rinder et al., "Effects of Meloxicam on Platelet Function in Healthy Adults: A Randomized, Double-Blind, Placebo-Controlled Trial", J Clin Pharmacol, 2002, 42, pp. 881-886.

Romsing et al., "Postoperative Analgesia is not Different After Local vs Systemic administration of Meloxicam in Patients Undergoing Inguinal Hernia Repair", Can H Anesth, 2001, 48(10), pp. 978-984.

(Continued)

*Primary Examiner* — Susan T Tran
(74) *Attorney, Agent, or Firm* — Stradley Ronon Stevens & Young, LLP

(57) ABSTRACT

The present invention is directed to nanoparticulate compositions comprising meloxicam particles having an effective average particle size of less than about 2000 nm.

4 Claims, 5 Drawing Sheets

(56) References Cited

U.S. PATENT DOCUMENTS

| | | |
|---|---|---|
| 5,573,749 A | 11/1996 | Illig |
| 5,573,750 A | 11/1996 | Singh |
| 5,573,783 A | 11/1996 | Desieno et al. |
| 5,581,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,097 A | 1/1997 | Corbin |
| 5,622,938 A | 4/1997 | Wong |
| 5,628,981 A | 5/1997 | Liversidge et al. |
| 5,643,552 A | 7/1997 | Illig |
| 5,662,883 A | 9/1997 | Bagchi et al. |
| 5,665,331 A | 9/1997 | Bagchi et al. |
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,776,496 A | 7/1998 | Violante et al. |
| 5,834,025 A | 11/1998 | De Garavilla et al. |
| 5,861,426 A | 1/1999 | Del Soldata et al. |
| 5,862,999 A | 1/1999 | Czekai et al. |
| 6,045,829 A | 4/2000 | Liversidge et al. |
| 6,068,858 A | 5/2000 | Liversidge et al. |
| 6,153,225 A | 11/2000 | Lee et al. |
| 6,165,506 A | 12/2000 | Jain et al. |
| 6,184,220 B1 | 2/2001 | Turck et al. |
| 6,221,377 B1 | 4/2001 | Meyer |
| 6,221,400 B1 | 4/2001 | Liversidge et al. |
| 6,264,922 B1 | 7/2001 | Wood et al. |
| 6,267,989 B1 | 7/2001 | Liversidge et al. |
| 6,270,806 B1 | 8/2001 | Liversidge et al. |
| 6,284,269 B1 | 9/2001 | Struengmann et al. |
| 6,316,029 B1 | 11/2001 | Jain et al. |
| 6,375,986 B1 | 4/2002 | Ryde et al. |
| 6,428,814 B1 | 8/2002 | Bosch |
| 6,431,478 B1 | 8/2002 | Reed et al. |
| 6,432,381 B2 | 8/2002 | Liversidge et al. |
| 6,479,551 B1 | 11/2002 | Plachetka et al. |
| 6,582,285 B2 | 6/2003 | Czekai et al. |
| 6,592,903 B2 | 7/2003 | Ryde et al. |
| 6,656,504 B1 | 12/2003 | Bosch et al. |
| 6,908,626 B2 | 6/2005 | Cooper et al. |
| 8,512,727 B2* | 8/2013 | Cooper ............... A61K 9/145 424/422 |
| 2002/0012675 A1 | 1/2002 | Jain et al. |
| 2002/0019431 A1 | 2/2002 | Straub et al. |
| 2002/0028238 A1 | 3/2002 | Karim et al. |
| 2002/0035107 A1 | 3/2002 | Henke et al. |
| 2002/0035264 A1 | 3/2002 | Kararli et al. |
| 2002/0077328 A1 | 6/2002 | Hassan et al. |
| 2002/0102280 A1 | 8/2002 | Anderson |
| 2003/0119825 A1 | 6/2003 | Folger et al. |
| 2003/0137067 A1* | 7/2003 | Cooper ............... A61K 9/146 264/5 |
| 2004/0122011 A1 | 6/2004 | Masferrer et al. |
| 2004/0229038 A1 | 11/2004 | Cooper |
| 2008/0102121 A1 | 5/2008 | Devane et al. |
| 2008/0214538 A1 | 9/2008 | Bourrie et al. |
| 2010/0137292 A1 | 6/2010 | Turp et al. |
| 2010/0316725 A1 | 12/2010 | Ryde |

FOREIGN PATENT DOCUMENTS

| | | |
|---|---|---|
| EP | 0499299 A2 | 8/1992 |
| EP | 0577215 | 1/1994 |
| EP | 0945131 | 9/1999 |
| WO | 9325190 | 12/1993 |
| WO | 9524339 | 8/1996 |
| WO | 9909988 | 3/1999 |
| WO | 0072973 | 12/2000 |
| WO | 0145706 | 12/2000 |
| WO | 2001021154 A2 | 3/2001 |
| WO | 02094215 | 11/2002 |
| WO | 02098565 | 12/2002 |
| WO | 2005105101 A1 | 11/2005 |
| WO | 2006000306 A1 | 1/2006 |

OTHER PUBLICATIONS

Schmid et al., "Pharmacokinetics and Metabolic Pattern after Intravenous Infusion and Oral Administration to Healthy Subjects", 1995, pp. 1206-1213.
Singh et al., "Risk of Serious Upper Gastrointestinal and Cardiovascular Thromboembolic Complications with Meloxicam", 2004, pp. 100-106.
Stet et al., "Local Tissue Tolerability of Meloxicam, A New NSAID: Indications of Parenteral Dermal and Mucosal Administration", British Journ of Rheumatology, 1996, 35(Suppl. 1), pp. 44-50.
Strand, "Are COX-2 Inhibitors Preferable to Non-Selective Non-Steroidal Anti-Inflammatory Drugs in Patients with Risk of Cardiovascular Events Taking Low-Dose Aspirin?", Lancet, 2007, pp. 2138-2151.
Sunshine et al., "Analgesic Efficacy of a Hydrocodone with Ibuprofen Combination Compared with Ibuprofen Alone for the Treatment of Acute Postoperative Pain", J Clin Pharmacol, 1997, 37, pp. 908-915.
Swamy et al., "Orodispersible Tablets of Meloxicam using Disintegrant Blends for Improved Efficacy", Indian Journ of Pharm Sci, 2007, pp. 836-841.
Thompson et al., "Effect of Meloxicam on Postoperative Pain After Abdominal Hysterectomy", British Journ of Anaesth, 2000, 84(2), pp. 151-154.
Thwaites et al., "Intravenous Ketorolac Tromethamine Does not Worsen Platelet Function During Knee Arthroscopy Under General Anesthesia", Anesth Analg, 1995, 81, pp. 119-124.
Thwaites et al., "Intravenous Ketorolac Tromethamine Worsens Platelet Function During Knee Arthroscopy Under General Anesthesia", Anesth Analg, 1996, 82, pp. 1176-1181.
Turck et al., "Clinical Pharmacokinetics of Meloxicam", Arzneim-Forsch/Drug Res, 1997, 47(1), pp. 253-258.
Van Hecken et al., "Comparative Inhibitory Activity of Rofecoxib, Meloxicam, Diclofenac, Ibuprofen, and Naproxen on COX-2 versus COX-1 in Healthy Volunteers", J. Clin Pharm, 2000, 40, pp. 1109-1120.
Van Kraaij et al., "A comparison of the effects of nabumetone vs. meloxicam on serum thromboxane B2 and platelet function in healthy volunteers", 2002, pp. 644-647.
Weber et al., "COX 2 selectivity of non-steroidal anti-inflammatory drugs and perioperative blood loss in hip surgery. A randomized comparison of indeomethacin and meloxicam", 2003, pp. 963-966.
Wideman et al., "Analgesic Efficacy of a combination of hydrocodone with ibuprofen in postoperative pain", 1999, pp. 66-76.
Zeienakas et al., "Analgesic efficacy of single oral doses of lumiracoxib and ibuprofen in patients with postoperative dental pain", J Clin Pract, 2004, 58(3), pp. 251-256.
Gravestock, Analytical Service Report, Meloxicam pKa and Solubility Analysis, 2008, pp. 1-7.
Gravestock, Meloxicam Aq GI-Dissolution, 2008, pp. 1-3.
Dreiser et al., "Oral meloxicam is effective in acute sciatica: two randomized, double-blind trails versus placebo or diclofenac", Inflamm Res, 2001, 50(Suppl 1), pp. S17-S23.
Akarsu et al., "Preemptive meloxicam for postoperative pain relief after abdominal hysterectomy", Clin Exp Obstet Gynecol, 2004, 31(2), pp. 133-136.
De Mello et al., "Double-blind study to evaluate efficacy and safety of meloxicam 7.5 mg and 15 mg versus mefenamic acid 1500 mg in the treatment of primary dysmenorrheal", Acta Obstet Gynecol Scand, 2004, 83(7), pp. 667-673.
Cheng et al., "A single-blind, randomized, controlled trial to assess the efficacy and tolerability of rofecoxib, diclofenac sodium, and meloxicam in patients with acute gouty arthritis", Clin Ther, 2004, 26(3), pp. 399-406.
Carroll et al., "Analgesic efficacy of preoperative administration of meloxicam or butorphanol in onychectomized cats", J Am Vet Med Assoc, 2005, 226(6), pp. 913-919.

(56) References Cited

OTHER PUBLICATIONS

Deneuche et al., "Analgesic comparison of meloxicam or ketoprofen for orthopedic surgery in dogs", Vet Surg, 2004, 33(6), pp. 650-660.
Fowler et al., "An evaluation of the analgesic effects of meloxicam in addition to epidural morphine/mepivacaine in dogs undergoing cranial cruciate ligament repair", Can Vet J, 2003, 44(8), pp. 643-648.
Caulkett et al., "A comparison of the analgesic effects of butorphanol with those of meloxicam after elective ovariohysterectomy in dogs", Can Vet J, 2003, 44(7), pp. 565-570.
Budsberg et al., "Evaluation of Intravenous administration of meloxicam for perioperative pain management following stifle joint surgery in dogs", Am J Vet Res, 2002, 63(11), pp. 1557-1563.
Lascelles et al., "Evaluation of the clinical efficacy of meloxicam in cats with painful locomotor disorders", J Small Anim Pract, 2001, 42(12), pp. 587-593.
Mathews et al., "Safety and efficacy of preoperative administration of meloxicam, compared with that of ketoprofen and butorphanol in dogs undergoing abdominal surgery", Am J Vet Res, 2001, 62(6), pp. 882-888.
Scientific Discussion, EMEA, 2007, pp. 1-96.
International Search Report for related International Patent Application No. PCT/US2010/036304, completed Sep. 10, 2010.
Written Opinion for related International Patent Application No. PCT/US2010/036304, completed Sep. 10, 2010.
Hintz et al., "The Effect of Particle Size distribution on Dissolution Rate and Oral Absorption", Intern Journ of Pharm, 1989, 51, pp. 9-17.
Office Action cited in related U.S. Appl. No. 10/784,900, dated Feb. 15, 2011.
Office Action cited in related U.S. Appl. No. 10/784,900, dated Sep. 29, 2011.
Office Action cited in related U.S. Appl. No. 10/784,900, dated Apr. 10, 2012.
Office Action cited in related U.S. Appl. No. 10/784,900, dated May 26, 2010.
The Physicians' Desk Reference, 56th Ed., 2002, pp. 1054.
The Merck Index, 13th Ed., 2001, pp. 1040-1041.
Lees et al., Brit Vet J, 1991, 147, pp. 97.
Henderson et al., Prakt Tierarzt, 1994, 75, pp. 179.
Tsai et al., Hely Chim Acta, 1993, 76, pp. 842.
Brit J Rheumatol, 1996, 35(Suppl.1), pp. 1-77.
Hawkey et al., Brit J Rheumatol, 1998, 37, pp. 937.
Dequeker et al., Brit J Rheumatol, 1998, 37, pp. 946.
Vane et al., Proc Natl Acad Sci USA, 1994, 91, pp. 2046-2050.
Oulette et al., Proc Natl Acad Sci, 2001, 98, pp. 14583-14588.
Selbert et al., Proc Natl Acad Sci, 1994, 91, pp. 12013-12017.
Final Office Action cited in related U.S. Appl. No. 15/437,534, dated Jun. 26, 2018.
Smith et al., Proc Natl Acad Sci, 1998, 95, pp. 13313-13318.
Notice of Reasons for Rejections cited in related Japanese Patent Application No. 2006-532300, completed Apr. 21, 2010.
Notice of Reasons for Rejections issued in related Japanese Patent Application No. 2010-233858, dated Oct. 17, 2012.
Rasenack et al., "Micro and the Importance of Nanoparticles of Pharmacy particle size", PZ Prisma, 2002, 9(3), pp. 183-190.
European Office Communication cited in related European Patent Application No. 08006465.2, dated Oct. 2, 2012.
Declaration of David S. Manswer in the matter of EP 04785761 dated Sep. 26, 2008.
Aulton, "Pharmaceuticals: The Science of Dosage Form Design", 1998, p. 71.
European Patent Application Np. EP 09006465.2 Oral Summons to Attend Oral Proceedings dated Apr. 14, 2015.
Ahmed et al., "Meloxicam in rheumatoid arthritis", 2005, pp. 739-751.
Altman et al., "Efficacy Assessment of Meloxicam, a Preferential Cyclooxygenaise-2 Inhibitor, in Acute Coronary Syndromes without ST-Segment Elevation", 2002, pp. 191-195.

Aoki et al., "Premedication with cyclooxygenase-2 inhibitor meloxicam reduced postoperative pain in patients after oral surgery", 2006, pp. 613-617.
Auvinet et al., "Comparison of the Onset and Intensity of Action of Intramuscular Meloxicam Oral Meloxicam in Patients with Acute Sciatica", Clin Therap, 1995, 17(6), pp. 1078-1090.
Barner, "Review of Clinical Trails and Benefit/Risk Ratio of Meloxicam", 1996, pp. 29-37.
Bosch et al., "Efficacy and Tolerability of Intramuscular and Oral Meloxicam in Patients with Acute Lumbago: A Comparison with Intramuscular and Oral Piroxicam", 1997, pp. 29-38.
Busch et al. "Pharmacokinetics of Meloxicam in Animals and the Relevance to Humans", Drug Metabolism and Disposition, 1998, 26(6), pp. 576-584.
Calvo et al., "Analgesic and anti-inflammatory dose-response relationship of 7.5 and 15 mg meloxicam after lower third molar removal: a double-blind, randomized, crossover study", Int J Oral Maxillofac Surg, 2007, 36, pp. 26-31.
Chen et al., "Cyclooxygenase-2 selective non-steroidal anti-inflammatory drugs (etodalac, meloxicam, celecoxib, rofecoxib, etoricoxib, valdecoxib and lumiracoxib) for osteoarthritis and rheumatoid arthritis: a systematic review and economic evaluation", 2008, 12(11), pp. 4.
Chung, "The Use of Injectable Nonsteroidal Anti-Inflammatory Drugs in Local Accident & Emergency Practice", Hong King Journ of Emerg Med, 2002, pp. 65-71.
Colberg et al., "The efficacy and tolerability of an 8-day administration of intravenous and oral meloxicam: a comparison with intramuscular and oral diclofenac in patients with acute lumbago", Current Medical Research and Opin, 1996, 13(7), pp. 363-377.
Combe et al., "Comparsion of Intramuscular and Oral Meloxicam in Rheumatoid Arthritis Patients", 2001, pp. 10-16.
Davies et al., "Clinical Pharmacokinetics of Meloxicam", 1999, pp. 115-126.
DeAndradre et al., "Ketoroiec Versus Meperidine for Pain Relief After Orthopaedic Surgery", 1996, pp. 302-312.
Degner et al., "Pharmacological, Pharmacokinetic and Clinical Profile of Meloxicam", Drugs of Today, 1997, 33(10), pp. 739-758.
Del Tacca et al., "Efficacy and Tolerability of Meloxicam, a COX-2 Preferential Nonsteroidal Anti-Inflammatory Drug", Clin Drug Invest, 2002, 22(12), pp. 799-818.
Engelhardt, "Meloxicam Inhibits Preferentially COX-2", Euro Journ of Pharm, 1994, Abstracts of 4th Annual Meeting of the German Society of Clin Pharmacology and Therapy, pp. 2.
Euller-Ziegler et al., "Meloxicam: a review of its pharmacokinetics, efficacy and tolerability following intramuscular administration", 2001, pp. 5-9.
Filatova et al., "Efficacy of movalis in the treatment of acute low back pains", 2005, pp. 33-37.
Furst, "Meloxicam: Selective COX-2 Inhibitation in Clinical Practice", 1997, pp. 21-27.
Sates et al., "Meloxicam: a reappraisal of Pharmacokinetics, efficacy and safety", 2005, pp. 2117-2140.
Gebuhr et al., "A Multiple-dose, Double-blind Comparison of Intramuscularly and Orally Administered Ketorolac Tromethamine and Ketogan in Patients with Pain Following Orthopaedic Surgery", 1994, pp. 202-217.
Ghozlan et al., "Tolerability of Multiple Administration of Intramuscular Meloxicam: A Comparison with Intramuscular Piroxicam in patients with rheumatoid arthritis or osteoarthritis", 1996, pp. 51-55.
Gillis et al., "Ketorolac: A Reappraisal of its Pharmacodynamic and Pharmacokinetic Properties and Therapeutic Use in Pain Management", Drugs, 1997, 53(1), pp. 139-168.
Haas et al., "An Update on Analgesics for the Management of Acute Postoperative Dental Pain", Journ of the Canadian Dental Assoc, 2002, 68(8), pp. 476-482.
Hawkey et al., "Gastrointestinal Tolerability of Meloxicam Compared to Diclofenac in Osteoarthritis Patients", British Society for Rheumatology, 1998, pp. 937-945.

(56) References Cited

OTHER PUBLICATIONS

Hill et al., "Analgesic Efficacy of the Cyclooxygenase-Inhibiting Nitric Oxide Donor AZD3582 in Postoperative Dental Pain: Comparison with Naproxen and Rofecoxib in Two Randomized Double-Blind, Placebo-Controlled Studies", Clinical Therapeutics, 2006, 28(9), pp. 1279-1295.

Hinz et al., "Can Drug Removals Involving Cyclooxygenase-2 Inhibitors be Avoided? A Plea for Human Pharmacology", Trends in Pharmacological Sciences, 2008, pp. 391-397.

Hosein et al., "Evaluation of Meloxicam (A Cox-2 Inhibitor) for Management of Postoperative Endodontic Pain: A Double-blind Placebo-controlled Study", Journ of Encodontics, 2003, pp. 634-637.

Issioui et al., "The Efficacy of Premedication with Celecoxib and Acetaminophen in Preventing Pain After Otolaryngologic Surgery", Anesh Analog, 2002, pp. 1188-1193.

Jick, "The Risk of Gastrointestinal Bleed, Myocardial Infarction and Newly Diagnosed Hypertension in Users of Meloxicam, Diclofenac, Naproxen, and Piroxicam", Pharmacotherapy, 2000, 20(7), pp. 741-744.

Kurukahvecioglu et al., "Effect of Meloxicam on Postoperative Pain Relief after Inguinal Hernia Repair with Local Anaesthesia", West Indian Med J, 2007, 56(6), pp. 530-533.

Lugar et al., Structure and physicochemical properties of meloxicam, a new NSAID, 1996, pp. 175-187.

Malan et al., "The Cyclooxygenase-2 Specific Inhibitor Paracoxib Sodium is as Effective as 12 mg of Morphone Administered Intramuscularly for Treating Pain After Gynecologic Laparotomy Surgery", Anesth Analg, 2005, pp. 454-460.

Mazurov et al., "Use of meloxicam (movalis) in patients with rheumatic diseases with concomitant coronary heart disease", Klin Med (Mosk), 2004, 82(12), pp. 54-59.

Mitchell et al., "Clinico-pharmacological studies on Ketoprofen ('Orudis')", 1975, pp. 423-430.

Naidu et al., "Physicochemical characterization and dissolution properties of meloxicam-cyclodextrin binary systems", 2004, pp. 75-86.

Narjes et al., "Pharmacokinetics and tolerability of meloxicam after i.m. administration", Br J Clin Pharm, 1996, 41, 135-139.

Narjes et al., "Parenteral Tolerability of Meloxicam in Healthy Volunteers", p. 61.

Nekoofar et al., "Evaluation of Meloxicam (A COX-2 Inhibitor) for Management of Postoperative Endodontic Pain: A Double-blind Palcebo-controlled Study", Journ of Endodontics, 2003, 29(10), pp. 634-637.

Nikanne et al., "Comparison of perioperative ketoprofen 2.0 mg kg-1 with 0.5 mg kg-1 i.v. in small children during adenoidectomy", British Journ of Anaesthesia, 1997, 79, pp. 606-608.

Odinak et al., "Use of Movalis in Treatment of Dorsophathy", 2004, pp. 29-32.

Palangio et al., "Combination Hydrocodone and Ibuprofen Versus Combination Oxycodone and Acetaminophen in the Treatment of Postoperative Obstetric of Gynecologic Pain", Clin Therapeutics, 2000, 22(5), pp. 600-612.

Pallapies et al., "Effects on Platelet Functions and Pharmacokinetics of Azapropazone and Ketoroiac Tromethaminz Given as Single Parenteral Doses", 1993, pp. 335-339.

Panara et al., "Dose-Dependent Inhibition of Platelet Cyclooxygenase-1 and Monocyte Cyclooxygenase-2 by Meloxicam in Healthy Subjects", 1999, pp. 276-280.

Power et al., "Comparison of I.M. Ketoroiac Trometamol and Morphine Sulphate for Pain Relief after Cholecystectomy", British Journ of Anaesthesia, 1990, 65, pp. 448-455.

Rani et al., "Determination of Oral Meloxicam Pharmacokinetic Parameters in Asian Indians: Comparison with a German Population", Saudi Pharm J, 2004, 12(4), pp. 144-149.

Notice of Allowance dated Nov. 14, 2018 in corresponding U.S. Appl. No. 15/950,539.

Office Action dated Sep. 26, 2018 in related U.S. Appl. No. 15/437,534.

Official Action dated Feb. 26, 2019 in corresponding U.S. Appl. No. 15/950,539.

Office Action cited in related U.S. Appl. No. 15/950,539, dated Apr. 11, 2018.

Notice of Allowance dated Jun. 14, 2019 in corresponding U.S. Appl. No. 15/437,534.

\* cited by examiner

NANOPARTICULATE MELOXICAM FORMULATIONS

CROSS-REFERENCE TO RELATED APPLICATIONS

This application is a continuation of U.S. patent application Ser. No. 15/437,534, filed Feb. 21, 2017, which is a continuation of U.S. patent application Ser. No. 13/941,076, filed Jul. 12, 2013, which is a continuation of U.S. patent application Ser. No. 12/788,203, filed May 26, 2010, which is a continuation-in-part of U.S. patent application Ser. No. 10/784,900, filed Feb. 24, 2004, now U.S. Pat. No. 8,512,727 issued Aug. 20, 2013, which claims priority to U.S. Provisional Patent Application No. 60/450,705, filed Mar. 3, 2003. The contents of these applications are incorporated herein by reference in their entirety.

BACKGROUND OF THE INVENTION

Nanoparticulate active agent compositions are described in U.S. Pat. No. 5,145,684 ("the '684 patent") as particles comprising a poorly soluble therapeutic or diagnostic agent having adsorbed onto or associated with the surface thereof a non-crosslinked surface stabilizer.

Methods of making nanoparticulate active agent compositions are described in, for example, U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−) Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive Nanoparticulate Compositions Having Cationic Surface Stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract," U.S. Pat. No. 6,592,903 for "Nanoparticulate Dispersions Comprising a Synergistic Combination of a Polymeric Surface Stabilizer and Dioctyl Sodium Sulfosuccinate," U.S. Pat. No. 6,582,285 for "Apparatus for sanitary wet milling;" U.S. Pat. No. 6,656,504 for "Nanoparticulate Compositions Comprising Amorphous Cyclosporine;" U.S. Pat. No. 6,742,734 for "System and Method for Milling Materials;" U.S. Pat. No. 6,745,962 for "Small Scale Mill and Method Thereof;" U.S. Pat. No. 6,811,767 for "Liquid droplet aerosols of nanoparticulate drugs;" U.S. Pat. No. 6,908,626 for "Compositions having a combination of immediate release and controlled release characteristics;" U.S. Pat. No. 6,969,529 for "Nanoparticulate compositions comprising copolymers of vinyl pyrrolidone and vinyl acetate as surface stabilizers;" and U.S. Pat. No. 6,976,647 for "System and Method for Milling Materials," U.S. Pat. No. 6,991,191 for "Method of Using a Small Scale Mill;" U.S. Pat. No. 7,101,576 for "Nanoparticulate Megestrol Formulation," U.S. Pat. No. 7,198,795 for "In vitro methods for evaluating the in vivo effectiveness of dosage forms of microparticulate of nanoparticulate active agent compositions;" U.S. Pat. No. 7,244,451 for "Methods of making nanoparticulate drug compositions comprising copolymers of vinyl pyrrolidone and vinyl acetate as surface stabilizers"; U.S. Pat. No. 7,276,249 for "Nanoparticulate Fibrate Formulations"; U.S. Pat. No. 7,288,267 for "Bioadhesive nanoparticulate compositions having cationic surface stabilizers"; U.S. Pat. No. 7,320,802 for "Methods of treatment using nanoparticulate fenofibrate compositions"; and U.S. Pat. No. 7,390,505 for "Nanoparticulate topiramate formulations", all of which are specifically incorporated by reference.

Meloxicam, also known as 4-hydroxy-2-methyl-N-(5-methyl-2-thiazolyl)-2-H-1,2-benzothiazine-3-carboxamide 1,1-dioxide, is a member of the enolic acid group of non-steroidal anti-inflammatory drugs (NSAIDs). Meloxicam is an oxicam derivative with the following chemical structure:

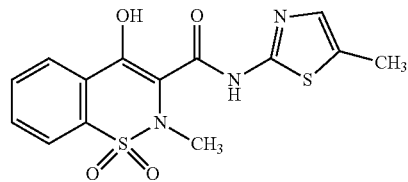 [SMILES: Cc1cnc(NC(=O)C2=C(O)c3ccccc3S(=O)(=O)N2C)s1]

Meloxicam has an empirical formula of $C_{14}H_{13}NO_4S_2$ and a molecular weight of 351.41. See The Physicians' Desk Reference, 56th Ed., pp. 1054 (2002); and The Merck Index, 13th Ed., pp. 1040-1041 (Merck & Co. 2001). Meloxicam is practically insoluble in water with higher solubility observed in strong acids and bases. It is very slightly soluble in methanol. The Physicians' Desk Reference, 56th Ed., pp. 1054.

4-hydroxy-2H-1,2-benzothiazine-3-carboxamide-1,1-dioxides and salts thereof, as well as methods of preparing these compounds, pharmaceutical compositions containing them as active ingredients, and methods of using them as antiphlogistics, are discussed in U.S. Pat. No. 4,233,299, herein in corporated by reference. The pharmacology of meloxicam in horses is discussed in Lees et al., Brit. Vet. J., 147: 97 (1991); veterinary trials in dogs are discussed in Henderson et al., Prakt. Tierarzt., 75:179 (1994); the physiochemical properties of meloxicam are discussed in Tsai et al., Helv. Chim. Acta, 76:842 (1993); the pharmacology, mechanism of action, and clinical efficacy are discussed in Brit. J. Rheumatol., 35(Suppl. 1): 1-77 (1996); and clinical trials of gastrointestinal tolerability in arthritis is discussed in Hawkey et al., Brit. J. Rheumatol., 37:937 (1998), and Dequeker et al., Brit. J. Rheumatol., 37:946 (1998).

Meloxicam exhibits anti-inflammatory, analgesic, and antifebrile activities. Like other NSAIDs, the primary mechanism of action of meloxicam is via inhibition of the cyclooxygenase (COX-2) enzyme system resulting in decreased prostaglandin synthesis. See The Physicians' Desk Reference, 56th Ed., pp. 1054 (2002). In contrast, COX-2 is not present in healthy tissue and its expression is induced in certain inflammatory states. See Vane et al., Proc. Natl. Acad. Sci. USA, 91:2046-2050 (1994); Oulette et al., Proc. Natl. Acad. Sci., 98:14583-14588 (2001); and Seibert et al., Proc. Natl. Acad. Sci., 91:12013-12017 (1994).

The pathological production of prostaglandins by COX-2 is implicated in a number of human disease states, including rheumatoid arthritis, osteoarthritis, pyrexia, asthma, bone resorption, cardiovascular diseases, nephrotoxicity, atherosclerosis, and hypotension. Id. Elevated levels of prostaglandins enhance or prolong pro-inflammatory signals which cause the pain, stiffness, and inflammation associated with these conditions. See Smith et al., Proc. Natl. Acad. Sci., 95:13313-13318 (1998).

Meloxicam is superior to traditional non-selective NSAIDs because it selectively inhibits COX-2, thus causing fewer gastrointestinal problems such as bleeding, heartburn, reflux, diarrhea, nausea, and abdominal pain. Meloxicam preferentially inhibits COX-2 with a COX-2/COX-1 inhibition ratio of 0.09. It is desirable to selectively inhibit COX-2 and the pathological production of prostaglandins for which that enzyme is responsible because the therapeutic analgesic/anti-inflammatory properties of NSAIDs occur by inhibition of inducible COX-2 at the site of inflammation. Conversely, the majority of adverse drug reactions to NSAIDs, including gastrointestinal ulcers and renal failure, result from inhibition of the constitutive COX-1 enzymes. This is because as a result of such COX-1 inhibition, prostaglandins necessary for gastric mucosal production and renal blood circulation are not produced. See Vane et al., Proc. Natl. Acad. Sci. USA, 91:2046 (1994); Oulette et al., Proc. Natl. Acad. Sci., 98:14583 (2001); and Seibert et al., Proc. Natl. Acad. Sci., 91:12013 (1994). Compounds that selectively inhibit the biosynthesis of prostaglandins by inhibiting the activity of the inducible enzyme, COX-2, exert anti-inflammatory effects without the adverse side effects associated with COX-1 inhibition.

Some of the trade names under which a commercially available meloxicam product has been or is marketed include MOBIC®, MOBEC®, MOBICOX®, MOVALIS®, and MOVATEC®. Meloxicam has been shown to be useful in the symptomatic treatment of painful osteoarthritis (arthrosis, degenerative joint disease), symptomatic treatment of rheumatoid arthritis, symptomatic treatment of ankylosing spondylitis, and symptomatic treatment of the signs and symptoms of osteoarthritis, including pain, stiffness, and inflammation.

The form of meloxicam currently marketed in the United States is MOBIC® (Boehringer Ingelheim Pharmaceuticals, Inc., Ridgefield, Conn.), provided in 7.5 and 15 mg tablets. The bioavailability of a single 30 mg oral dose is 89% as compared to a 30 mg intravenous bolus injection. The pharmacokinetics of a single intravenous dose of meloxicam is dose-proportional in the range of 5 to 60 mg. See The Physicians' Desk Reference, 56th Ed., pp. 1054 (2002). After administration of multiple oral doses of meloxicam, the pharmacokinetics is dose-proportional in the range of 7.5 to 15 mg. The rate or extent of absorption is not affected by multiple dose administration. Under fasted steady state conditions, the mean Cmax is achieved within four to five hours, with a second meloxicam concentration peak occurring at approximately twelve to fourteen hours post-dose, which suggests gastrointestinal recirculation. Under steady state fed conditions in healthy adult males, the 7.5 mg tablets have a mean Cmax of 1.05 μg/mL, a Tmax of 4.9 hrs, and a t½ of 20.1 hours. Under steady state fed conditions in elderly males and females, the 15 mg tablets have a Cmax of 2.3 and 3.2 μg/mL, respectively, a Tmax of 5 and 6 hrs, respectively, and a t½ of 21 and 24 hrs, respectively. See The Physicians' Desk Reference, 56th Ed., pp. 1054 (2002).

Meloxicam is useful in relieving the signs and symptoms of rheumatoid arthritis, lower back pain, and acute pain, e.g. treatment of post surgical pain, treatment of pain resulting from battle field wounds, and migraine headaches. Meloxicam may be especially effective for treatment of all types of pain associated with inflammation. In general meloxicam is effective for treatment of moderate to moderately severe acute pain as would be understood by a skilled practitioner.

NSAIDs, like meloxicam, are useful in pain management because NSAIDs provide an analgesic effect without the sedation and addictive properties of narcotic analgesics. Furthermore, the long $t_{1/2}$ of meloxicam makes it useful for long-lasting relief which is not provided by narcotic analgesics. However, due to their typically long onset of action, conventional NSAIDs, including conventional meloxicam, are frequently inappropriate for management of acute pain.

Because meloxicam is practically insoluble in water, attaining sufficient bioavailability of this drug is problematic. Prior art methods of increasing the bioavailability of meloxicam include increasing its solubility by forming a cyclodextrin complex of the drug (see U.S. Pat. No. 6,284,269) or by forming a salt of meloxicam with an inorganic or organic base (U.S. Pat. Appln. Pub. No. US 2002/0035107 A1).

The skilled person knows that for any particulate composition to be approved by the FDA for intravenous (I.V.) or intramuscular (I.M.) administration, the composition must meet the standards set forth in General Chapter 788 of the United States Pharmacopoeia ("USP<788>"). Specifically, in the United States, any particulate matter injectable solution must comply with the particle size and number requirements of USP<788>. That is, under the approved "Light Obscuration" test set forth in USP<788>, known as "Method 1," there must be: (i) no more than 6,000 particles in a particulate composition that are greater than 10 μm in size and (ii) no more than 600 particles that are greater than 25 μm in size. Under "Method 2," the Microscopy test, a particulate composition must contain (i) no more than 3,000 particles in a particulate composition that are greater than 10 μm in size and (ii) no more than 300 particles that are greater than 25 μm in size. The theorized large particles represent the presence of aggregates of individual particles which clump together.

Because poorly water soluble active agents are difficult to solubilize in an aqueous based mammal environment, it can be difficult to formulate many poorly water soluble drugs for injectable formulations as conventional poorly water soluble drug formulations can contain particles of drug which do not meet the standards set forth in USP<788>. This is problematic, as an injectable formulation may be highly desirable over an alternative dosage form. For example, drugs taken orally may cause significant first pass liver damage, which can be avoided or minimized using an injectable dosage form. Particularly for pain medication, injectable dosage forms may be highly desirable due to the fast onset of activity.

BRIEF SUMMARY OF THE INVENTION

The present invention is directed to a method of treating moderate to moderately severe acute pain with a composition comprising meloxicam. In an exemplary embodiment, method of treatment includes administering an injectable dosage form comprising meloxicam, polyvinylpyrrolidone, NaDOC, and sucrose to a patient in need thereof. In an embodiment of the invention, the composition provides meaningful pain relief for up to 24 hours when administered to a patient in need thereof.

BRIEF DESCRIPTION OF THE DRAWINGS

The invention is best understood from the following detailed description when read in connection with the accompanying drawings.

DETAILED DESCRIPTION OF THE INVENTION

Figure 1:
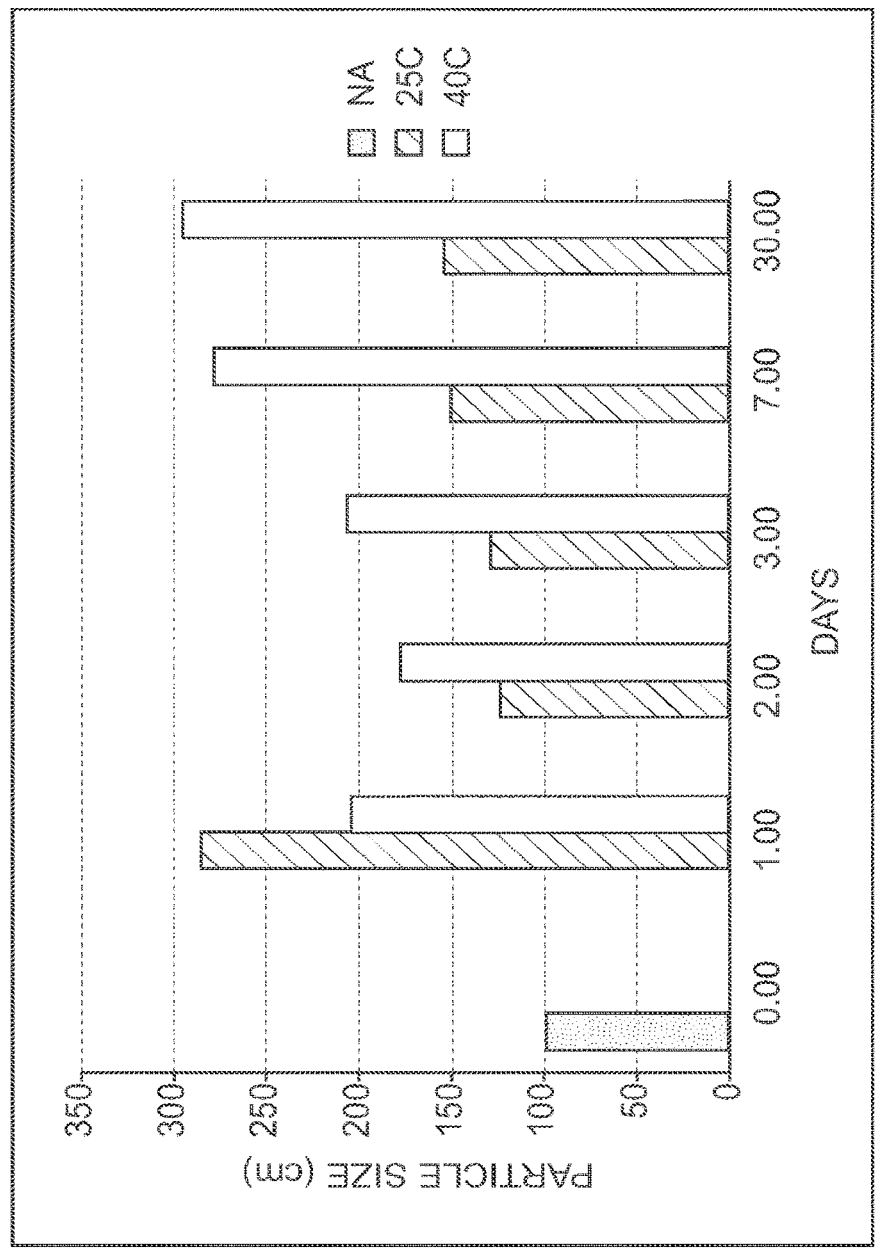
FIG. 1 is a particle size distribution plot of an exemplary embodiment of a formulation of the present invention stored at 25° C. and 40° C. for up to 30 days.
Figure 2:
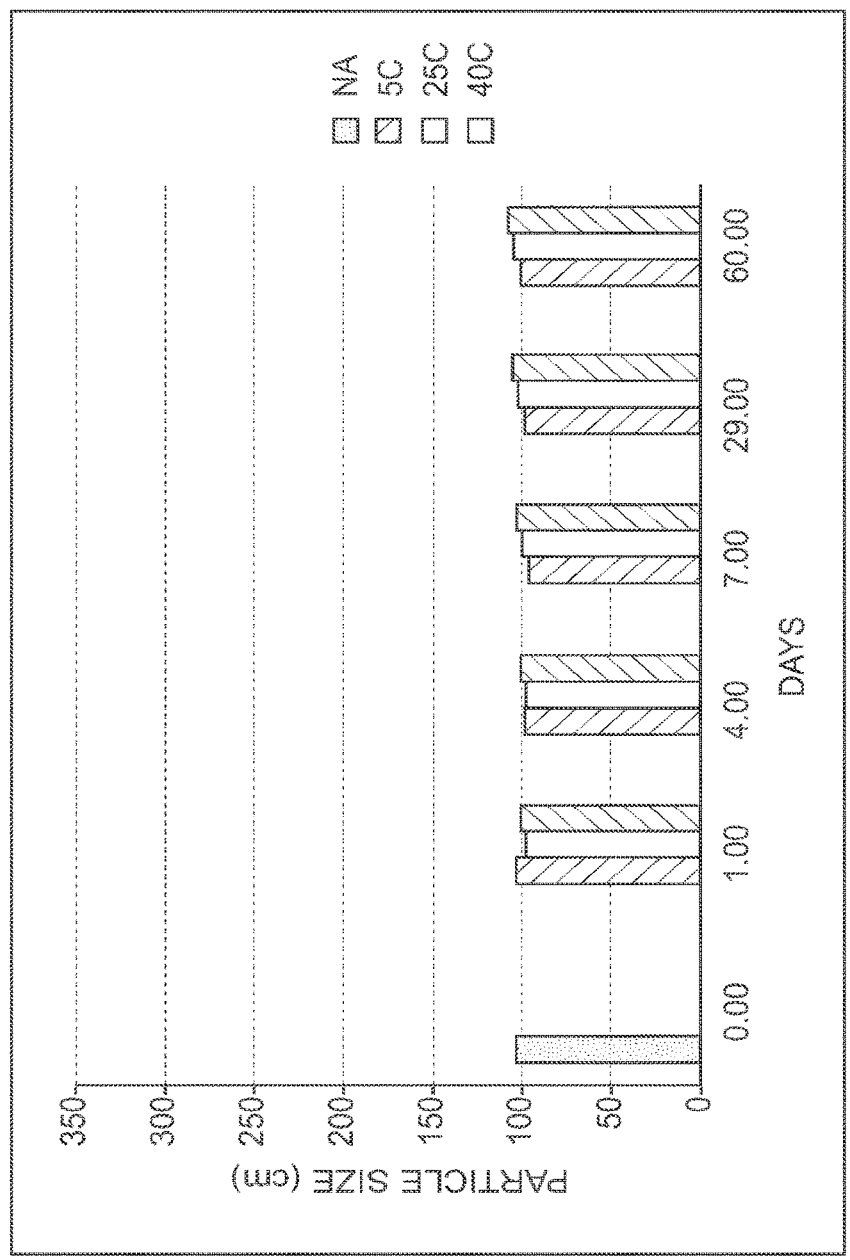
FIG. 2 is a particle size distribution plot of an exemplary embodiment of a formulation of the present invention stored at 5° C., 25° C. and 40° C. for up to 60 days.

The United States Food and Drug Administration (FDA) has defined bioequivalence as, "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study." (FDA, 2003) In other words, the FDA considers two products bioequivalent if the 90% CI of the relative mean $C_{max}$, $AUC_{(0-t)}$ and $AUC_{(0-\infty)}$ of the test formulation to reference formulation should be within 80.00% to 125.00%.

The present invention is directed to compositions comprising nanoparticulate meloxicam. The compositions comprise nanoparticulate meloxicam and at least one surface stabilizer adsorbed on the surface of the drug. The nanoparticulate meloxicam particles, which have an effective average particle size of less than about 2000 nm, surprisingly exhibit superior Tmax profiles as compared to conventional prior meloxicam formulations.

As taught in the '684 patent, not every combination of surface stabilizer and active agent will result in a stable nanoparticulate composition. It was surprisingly discovered that stable nanoparticulate meloxicam formulations can be made. As described in more detail below, preferred surface stabilizers include polyvinylpyrrolidone (e.g., Kollidon® 12 PF, Kollidon® 17 PF), docusate sodium, block polymers of polyethylene glycol and polypropylene glycol, poloxamers (e.g., Pluronics F68® and F108®, which are block copolymers of ethylene oxide and propylene oxide), polyethylene sorbitan monooleate (Polysorbate 80), sodium Deoxycholate, lecithin, lysozyme, and mixtures thereof. Docusate sodium is particularly useful as a surface stabilizer in combination with one or more other surface stabilizers.

As described in Example 3 below, many of these surface stabilizers are particularly suited for injectable nanoparticulate meloxicam formulations. This is significant, and surprising, as for injectable formulations it is critical that very small meloxicam particles be obtained. Moreover, the composition must be stable, with very little or no particle size growth observed, as injectable formulations having large particles can cause embolism.

Nanoparticulate meloxicam formulations suitable parenteral injection (e.g., intravenous, intramuscular, or subcutaneous) for the treatment of acute pain are highly superior to conventional meloxicam formulations because they have much faster onset of action due to the nanoparticulate size of the active agent.

In addition to exhibiting dramatically superior Tmax profiles, the nanoparticulate meloxicam formulations preferably also exhibit improved pharmacokinetic profiles as compared to conventional meloxicam formulations, resulting in faster onset of action and smaller effective doses as compared to prior conventional meloxicam formulations.

Conventional formulations of meloxicam are inappropriate for management of acute pain due to delayed onset of action, as such meloxicam formulations have a Tmax of 4-6 hours, which is more than five times as long as most narcotic analgesic drugs. See The Physician's Desk Reference, 56th Ed., pp. 446 and 1054. Unlike conventional meloxicam formulations, nanoparticulate meloxicam formulations, which exhibit faster onset of action, are useful in treating acute pain where fast pain relief is required.

Additionally, any drug, including meloxicam, can have adverse side effects. Thus, lower doses of meloxicam which can achieve the same or better therapeutic effects as those observed with larger doses of conventional meloxicam are desired.

Nanoparticulate formulations of meloxicam also provide a longer duration of pain relief as compared to traditional narcotic analgesic drugs. While traditional narcotics provide fast onset of action, the duration of pain relief is short. Nanoparticulate meloxicam formulations combine the fast onset of traditional narcotics with the duration of pain relief of conventional NSAIDs. The long half-life of meloxicam, approximately 20 hours as compared to 2-3 hours for most narcotics, confers a long duration of action and thus requires less frequent dosing.

Additionally, nanoparticulate meloxicam formulations do not possess the sedative and addictive properties of narcotic analgesics. Meloxicam does not cause drowsiness and is not addictive, making it a preferred analgesic when ambulation is important or when treatment is protracted and chemical dependency could result from continued use of narcotic analgesics.

Nanoparticulate formulations can be prepared for oral administration for treatment of, for example, migraine headaches. The use of oral nanoparticulate formulations also provide much faster onset of action as compared to conventional orally dosed meloxicam formulations.

In addition, the invention encompasses compositions comprising nanoparticulate meloxicam, one or more surface stabilizers, and one or more non-meloxicam active agents, either conventional or nanoparticulate. Methods of using such combination compositions are also encompassed by the invention. For example, additional analgesic drugs can be used in combination with nanoparticulate meloxicam, such as one or more COX-2 inhibitors, NSAIDs, or narcotics. Other exemplary types of active agents which can be used in combination with nanoparticulate meloxicam are described below. If the non-meloxicam active agent is in nanoparticulate form, then such a non-meloxicam active agent also has one or more surface stabilizers adsorbed onto the surface of the active agent. The surface stabilizer(s) adsorbed onto the surface of the non-meloxicam active agent can be the same as or different from the surface stabilizer(s) adsorbed onto the surface of the nanoparticulate meloxicam.

In general, such non-meloxicam active agents do not include vasomodulators, such as those described in U.S. Published Patent Application No. 20020077328.

In yet another embodiment of the invention, a first meloxicam formulation providing the pharmacokinetic profile required herein is co-administered with at least one other meloxicam formulation that generates a different pharmacokinetic profile, specifically one exhibiting slower absorption into the bloodstream and therefore a longer Tmax, and typically a lower Cmax. For example, the second meloxicam formulation can have a conventional particle size, which produces a longer Tmax, and typically a lower Cmax. Alternatively, a second, third, or fourth meloxicam formulation can differ from the first, and from each other, in the effective average particle sizes of each composition. The different particle sizes produce different Tmaxs. The combination of fast pain relief provided by the first formulation and longer-lasting pain relief provided by the second (or third, fourth, etc.) formulation can reduce the dose frequency required. Preferably where co-administration of a "fast-acting" formulation and a "longer-lasting" formulation is desired, the two formulations are combined within a single composition, for example a dual-release composition.

A. Compositions

The invention provides compositions comprising nanoparticulate meloxicam particles and at least one surface stabilizer. The surface stabilizers are adsorbed on the surface of the meloxicam particles. Surface stabilizers useful herein physically adhere on the surface of the nanoparticulate meloxicam but do not chemically react with the meloxicam particles or itself. Individually adsorbed molecules of the surface stabilizer are essentially free of intermolecular cross-linkages.

The invention also provides compositions of nanoparticulate meloxicam in combination with one or more conventional or nanoparticulate non-meloxicam drugs.

The present invention includes nanoparticulate meloxicam compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral (in solid, liquid, or aerosol form), vaginal, nasal, rectal, ocular, local (powders, ointments or drops), buccal, intracisternal, intraperitoneal, or topical administration, and the like. Such compositions can also comprise one or more conventional or nanoparticulate non-meloxicam drugs.

The present invention provides compositions of meloxicam with a desirable pharmacokinetic profile when administered to mammalian subjects. Preferably, the $T_{max}$ of a 7.5 mg orally administered dose of nanoparticulate meloxicam, when assayed in the plasma of a mammalian subject following administration of an initial dose, is less than about 5 hours, less than about 4 hours, less than about 3 hours, less than about 2 hours, less than about 1 hour, less than less than about 50 minutes, less than about 45 minutes, less than about 40 minutes, less than about 35 minutes, less than about 30 minutes, less than about 20 minutes, less than about 15 minutes, less than about 10 minutes, or less than about 5 minutes.

In addition, preferably the $C_{max}$ of a 7.5 mg orally administered dose of nanoparticulate meloxicam, when assayed in the plasma of a mammalian subject following administration of an initial dose, is greater than about 1 μg/mL, greater than about 3 μg/mL, greater than about 5 μg/mL, greater than about 10 μg/mL, or greater than about 15 μg/mL.

The desirable pharmacokinetic profile, as used herein, is the pharmacokinetic profile measured after the initial dose of meloxicam. The compositions can be formulated in any way as described below.

A preferred nanoparticulate meloxicam formulation of the invention exhibits in comparative pharmacokinetic testing with a standard commercial formulation of meloxicam, such as MOBIC® from Boehringer Ingelheim Pharmaceuticals, Inc., a Tmax not greater than about 90%, not greater than about 80%, not greater than about 70%, not greater than about 60%, not greater than about 50%, not greater than about 30%, not greater than about 25%, not greater than about 20%, not greater than about 15%, or not greater than about 10% of the Tmax exhibited by a standard commercial meloxicam formulation, e.g., MOBIC® tablets.

In addition, an exemplary oral nanoparticulate meloxicam formulation of the invention exhibits in comparative pharmacokinetic testing with a standard commercial formulation of meloxicam, such as MOBIC® from Boehringer Ingelheim Pharmaceuticals, Inc., a Cmax which is greater than about 20%, greater than about 40%, greater than about 60%, greater than about 80%, greater than about 100%, greater than about 140%, greater than about 180%, greater than about 200%, greater than about 240%, greater than about 280%, greater than about 300%, greater than about 340%, greater than about 380%, or greater than about 400% of the Cmax exhibited by a standard commercial meloxicam formulation, e.g., MOBIC® tablets.

Any nanoparticulate meloxicam formulation giving the desired pharmacokinetic profile is suitable for administration according to the present methods.

1. Meloxicam Particles

As used herein the term meloxicam, which is the active ingredient in the composition, is used to mean meloxicam (4-hydroxy-2-methyl-N-(5-methyl-2-thiazolyl)-2-H-1,2-benzothiazine-3-carboxamide 1,1-dioxide) or any salt thereof. Meloxicam can be present in a crystalline phase, an amorphous phase, or a mixture thereof.

Nanoparticulate meloxicam compositions are contemplated to be useful in treatment and/or prevention of a wide range of conditions and disorders mediated by COX-2, including but not limited to, disorders characterized by inflammation, pain, and/or fever. Such compositions are especially useful as anti-inflammatory agents, such as in treatment of arthritis, with the additional benefit of having significantly less harmful side effects than compositions of conventional NSAIDs that lack selectivity for COX-2 over COX-1. In particular, such compositions have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs.

Thus, nanoparticulate meloxicam compositions of the invention are particularly useful as an alternative to conventional nonnanoparticulate NSAIDs where such NSAIDs are contraindicated, for example in patients with peptic ulcers, gastritis, regional enteritis, ulcerative colitis, diverticulitis, or with a recurrent history of gastrointestinal lesions; gastrointestinal bleeding; coagulation disorders including anemia such as hypoprothrombinemia, hemophilia, or other bleeding problems; kidney disease; or in patients prior to surgery or patients taking anticoagulants.

Because of the rapid onset of therapeutic effect observed with the compositions of the invention, these compositions have particular advantages over prior conventional formulations for treatment of acute COX-2 mediated disorders, especially for relief of pain, for example in headache, including sinus headache and migraine.

Meloxicam is also useful in treating and/or preventing, for example, arthritic disorders, gastrointestinal conditions, inflammatory conditions, pulmonary inflammation, ophthalmic diseases, central nervous systems disorders, pain, inflammation-related cardiovascular disorders, angiogenesis-related disorders, benign and malignant tumors, adenomatous polyps, disorders of the female reproductive system such as endometriosis, osteoporosis, dysmenorrhea, premature labor, asthma, eosinophil-related disorders, pyrexia, bone resorption, nephrotoxicity, hypotension, arthrosis, joint stiffness, kidney disease, liver disease including hepatitis, acute mastitis, diarrhea, colonic adenomas, bronchitis, allergic neuritis, cytomegalovirus infectivity, apoptosis including HIV-induced apoptosis, lumbago; skin-related conditions such as psoriasis, eczema, acne, burns, dermatitis, and ultraviolet radiation damage including sunburn; allergic rhinitis, respiratory distress syndrome, and endotoxin shock syndrome. Nanoparticulate meloxicam is also useful as an immunosuppressive agent.

Exemplary forms of arthritic disorders which can be treated include, but are not limited to, osteoarthritis, rheumatoid arthritis, spondyloarthropathies, gouty arthritis, juvenile arthritis, gout, ankylosing spondylitis, systemic lupus erythematosus, bursitis, tendinitis, myofascial pain, carpal tunnel syndrome, fibromyalgia syndrome, infectious arthritis, psoriatic arthritis, reiter's syndrome, and scleroderma.

Exemplary gastrointestinal conditions or ulcerative diseases which can be treated include, but are not limited to, inflammatory bowel disease, Crohn's disease, gastritis, irritable bowel syndrome, ulcerative colitis, gastric ulcer, pathological but non-malignant conditions such as hemangiomas, including infantile hemaginomas, angiofibroma of the nasopharynx, and avascular necrosis of bone.

Exemplary inflammation conditions which can be treated include, but are not limited to, migraine headaches, periarteritis nodosa, thyroiditis, aplastic anemia, Hodgkin's disease, scleredoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, post-operative inflammation including that following ophthalmic surgery such as cataract surgery or refractive surgery, and the like.

Exemplary pulmonary inflammation conditions which can be treated include, but are not limited to, inflammation associated with viral infections and cystic fibrosis, and in bone resorption such as that associated with osteoporosis. Exemplary opthalmic diseases or conditions which can be treated include, but are not limited to, retinitis, conjunctivitis, retinopathies, uveitis, ocular photophobia, acute injury to the eye tissue, corneal graft rejection, ocular neovascularization, retinal neovascularization including neovascularization following injury or infection, diabetic retinopathy, macular degeneration, retrolental fibroplasia, glaucoma, and neovascular glaucoma. Exemplary central nervous system disorders which can be treated include, but are not limited to, cortical dementias including Alzheimer's disease, neurodegeneration, and central nervous system damage resulting from stroke, ischemia, and trauma. Exemplary pain conditions which can be treated include, but are not limited to, low back and neck pain, postoperative pain, pain resulting from battle field wounds, dental pain, muscular pain, pain resulting from cancer, headaches, including sinus headache and migraine, menstrual cramps, and pain associated with inflammation.

According to a preferred embodiment, the compositions of the invention are useful for treating moderate to moderately severe acute pain and/or prescribed for the management of severe pain as an adjunct therapy to opiod analgesics and may allow a reduction in the opiod dose and corresponding adverse events associated with opiod use. When the meloxicam composition of the present invention is formulated into an injectable dosage form and administered to a patient in need thereof, the composition of the invention provides a time to first perceptible pain relief. Time to first perceptible pain relief is the time from administration of the drug to the point at which the patient first perceives a change in their pain intensity (as discussed in Example 10). The time to perceptible pain relief ranges from about less than 1 minute, from about 1 to 30, 2 to 25, 5 to 20, 10 to 20 and 12 to 18 minutes. In other words, an injectable form of the present invention, when administered to a patient in need thereof, provides a time to first perceptible pain relief in about 30, 25, 20, 18, 16, 15, 14, 13, 12, 11, 10, 9, 8, 7, 6, 5, 4, 3, 2, 1 or less than 1 minute.

According to another embodiment, when the meloxicam composition of the present invention is formulated into an injectable dosage form and administered to a patient in need thereof, the composition of the invention provides a time to meaningful pain relief. Time to meaningful pain relief is the time from administration of the drug to the point at which the patient first perceives a meaningful reduction in pain intensity (as discussed in Example 10). The time to first meaningful pain relief ranges from about less than 25, from 25 to 300, 75 to 250, 100 to 200, and 115 to 125 minutes. In other words, an injectable form of the present invention, when administered to a patient in need thereof, provides a time to meaningful pain relief in about 300, 275, 250, 225, 200, 195, 185, 175, 165, 155, 150, 125, 100, 75, 50, 25, or less than 25 minutes.

According to yet another embodiment, when the meloxicam composition is formulated into an injectable dosage form and administered to a patient in need thereof, the composition of the invention provides meaningful pain relief for an extended period of time, such as, a period of up to 24 hours. According to other exemplary embodiments, the expended period of time that patients experience meaningful pain relief ranges from about 120 to 1440, 180 to 1320, 240 to 1260, 300 to 1200, 360 to 1140, 480 to 1080, 540 to 1020, 600 to 960, 660 to 900, or 720 to 840 minutes. In other words, an injectable form of the present invention, when administered to a patient in need thereof, provides a meaningful pain relief for up to about 120, 180, 240, 300, 360, 420, 480, 540, 600, 660, 720, 780, 840, 900, 960, 1020, 1080, 1140, 1200, 1260, 1320, or 1440 minutes. In a preferred embodiment, an exemplary method for treating moderate to moderately severe acute pain comprises administering to a patient in need thereof, an intravenous dosage form comprising 15 mg, 30 mg, or 60 mg, of meloxicam which provides a duration of analgesic effect for up to 1440 minutes (i.e., 24 hours).

Exemplary inflammation-related cardiovascular disorders which can be treated or prevented using the compositions of the invention include, but are not limited to, vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins, and capillaries.

In a preferred embodiment, meloxicam is useful for treating inflammation and pain in post-surgical settings. For example, one post surgical setting is post dental procedures, like extractions or molar insertions or bridge-work. Another surgical setting is post surgical soft tissue procedures, like abdominal surgeries involving appendectomies or gall bladder removals. Yet another post-surgical setting includes procedures related to bone manipulations, like hip, knee and shoulder surgeries.

Exemplary angiogenesis-related disorders include, but are not limited to, inhibition of tumor angiogenesis. Such compositions are useful in treatment of neoplasia, including metastasis, benign and malignant tumors, and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreatic cancer, ovarian cancer, prostate cancer, cervical cancer, lung cancer, breast cancer and skin cancer. The nanoparticulate meloxicam compositions of the invention can also be used to treat fibrosis that occurs with radiation therapy.

The compositions of the invention can be used to treat subjects having adenomatous polyps, including those with familial adenomatous polyposis (FAP). Additionally, such compositions can be used to prevent polyps from forming in patients at risk of FAP.

Because the meloxicam compositions of the invention inhibit prostanoid-induced smooth muscle contraction by inhibiting synthesis of contractile prostanoids, the compositions can be used in the treatment of dysmenorrhea, premature labor, asthma, and eosinophil-related disorders.

The compositions of the invention are also useful in treating indications where anti-inflammatory agents, anti-angiogenesis agents, antitumorigenic agents, immunosuppressive agents, NSAIDs, COX-2 inhibitors, analgesic agents, anti-thrombotic agents, narcotics, or antifebrile agents are typically used.

2. Non-Meloxicam Active Agents

The nanoparticulate meloxicam compositions of the invention can additionally comprise one or more non-meloxicam active agents, in either a conventional or nanoparticulate form. The non-meloxicam active agents, if present in nanoparticulate form, are present in a crystalline phase, a semi-crystalline, an amorphous phase, or a mixture thereof.

Such active agents can be, for example, an active, therapeutic, or diagnostic agent. A therapeutic agent can be a pharmaceutical agent, including biologics such as proteins, peptides, and nucleotides, or a diagnostic agent, such as a contrast agent, including x-ray contrast agents. The active agent can be selected from a variety of known classes of drugs, including, for example, proteins, peptides, nucleotides, anti-obesity drugs, nutraceuticals, dietary supplements, carotenoids, corticosteroids, elastase inhibitors, antifungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of active agents and a listing of species within each class can be found in Martindale's The Extra Pharmacopoeia, 31st Edition (The Pharmaceutical Press, London, 1996), specifically incorporated by reference. The active agents are commercially available and/or can be prepared by techniques known in the art.

Exemplary nutraceuticals and dietary supplements are disclosed, for example, in Roberts et al., Nutraceuticals: The Complete Encyclopedia of Supplements, Herbs, Vitamins, and Healing Foods (American Nutraceutical Association, 2001), which is specifically incorporated by reference. A nutraceutical or dietary supplement, also known as phytochemicals or functional foods, is generally any one of a class of dietary supplements, vitamins, minerals, herbs, or healing foods that have medical or pharmaceutical effects on the body. Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

Nanoparticulate meloxicam compositions useful in methods of the present invention can be used in combination therapies with opioids and other analgesics, including narcotic analgesics, Mu receptor antagonists, Kappa receptor antagonists, non-narcotic (i.e., non-addictive) analgesics, monoamine uptake inhibitors, adenosine regulating agents, cannabinoid derivatives, Substance P antagonists, neurokinin-1 receptor antagonists and sodium channel blockers, among others.

Preferred combination therapies comprise a composition useful in methods of the invention with one or more compounds selected from aceclofenac, acemetacin, e-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis(acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, α-bisabolol, bromfenac, p-bromoacetanilide, 5-bromosalicylic acid acetate, bromosaligenin, bucetin, bucloxic acid, bucolome, bufexamac, bumadizon, buprenorphinc, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamidc, crotcthamide, dcsomorphinc, dexoxadrol, dcxtromoramidc, dczocinc, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafeninc, glucamctacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phcnyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen, and zomepirac. See The Merck Index, 12th Edition (1996), Therapeutic Category and Biological Activity Index, lists therein headed "Analgesic", "Anti-inflammatory", and "Antipyretic").

Particularly preferred combination therapies comprise use of a nanoparticulate meloxicam composition of the invention with an opioid compound, more particularly where the opioid compound is codeine, meperidine, morphine, or a derivative thereof.

The compound to be administered in combination with a nanoparticulate meloxicam composition of the invention can be formulated separately from said composition or co-formulated with said composition. Where a meloxicam composition is co-formulated with a second drug, for example an opioid drug, the second drug can be formulated in immediate-release, rapid-onset, sustained-release, or dual-release form.

In an embodiment of the invention, particularly where the COX-2 mediated condition is headache or migraine, the nanoparticulate meloxicam composition is administered in combination therapy with a vasomodulator, preferably a xanthine derivative having vasomodulatory effect, more preferably an alkylxanthine compound.

Combination therapies wherein an alkylxanthine compound is co-administered with a nanoparticulate meloxicam composition as provided herein are embraced by the present embodiment of the invention whether or not the alkylxanthine is a vasomodulator and whether or not the therapeutic effectiveness of the combination is to any degree attributable to a vasomodulatory effect. The term "alkylxanthine" herein embraces xanthine derivatives having one or more C1-4 alkyl substituents, preferably methyl, and pharmaceutically acceptable salts of such xanthine derivatives. Dimethylxanthines and trimethylxanthines, including caffeine, theobromine, and theophylline, are especially preferred. Most preferably, the alkylxanthine compound is caffeine.

Exemplary COX-2 inhibitors which can be formulated in combination with the nanoparticulate meloxicam composition of the invention include, but are not limited to, celecoxib, rofecoxib (Vioxx®), meloxicam (MOBIC®, co-marketed by Abbott Laboratories, Chicago, Ill., and Boehringer Ingelheim Pharmaceuticals, Inc.), valdecoxib (G.D. Searle & Co.), parecoxib (G.D. Searle & Co.), MK-966 (Merck, in Phase HI studies), etoricoxib (MK-663; Merck, in Phase II studies), SC-236 (chemical name of 4-[5-(4-chlorophenyl)-3-(trifluoromethyl)-1H-pyrazol-1-yl)] benzenesulfonamide; G.D. Searle & Co., Skokie, Ill.); NS-398 (N-(2-cyclohexyloxy-4-nitrophenyl)methane sulfonamide; Taisho Pharmaceutical Co., Ltd., Japan); SC-58125 (methyl sulfone spiro (2.4)hept-5-ene I; Pharmacia/Searle & Co.); SC-57666 (Pharmacia/Searle & Co.); SC-58635 (celexcoxib; Pharmacia/Searle & Co.); SC-558 (Pharmacia/Searle & Co.); SC-560 (Pharmacia/Searle & Co.); etodolac (Lodine®, Wyeth-Ayerst Laboratories, Inc.); DFU (5,5-dimethyl-3-(3-fluorophenyl)-4-(4-methylsulfonyl)phenyl 2(5H)-furanone); MK-476, L-745337, L-761066, L-761000, L-748780, and L-748731 (all Merck & Co.); DUP-697 (5-Bromo-2-(4-fluorophenyl)-3-(4-(methylsulfonyl)phenyl; DuPont Merck Pharmaceutical Co.); PGV 20229 (1-(7-tert.-butyl-2,3-dihydro-3,3-dimethylbenzo(b)furan-5-yl)-4-cyclopropylbutan-1-one) (Procter & Gamble Pharmaceuticals); T-614 (3-formylamino-7-methylsulfonylamino-6-phenoxy-4H-1-benzopyran-4-one; Toyama Corp., Japan); BF 389 (Biofor, USA); PD 136005, PD 142893, and PD 145065 (all Parke-Davis/Warner-Lambert Co.); flurbiprofen (Ansaid®; Pharmacia & Upjohn); nimesulide (NIM-03, Mesulid®; Hisamitsu, Japan); nabumetone (Relafen®; SmithKline Beecham, plc); flosulide (CGP 28238; Novartis/Ciba Geigy); piroxicam (Feldene®; Pfizer); dicofenac (Voltaren® and Cataflam®, Novartis); COX-189 (Novartis); D 1367 (Celltech Chiroscience, plc); R 805 (4 nitro 2 phenoxymethane sulfonanilide); R 807 (3 benzoyldifluoromethane sulfonanilide, diflumidone); JTE-522 (Japan Tobacco, Japan); FK-3311 (4'-Acetyl-2'-(2,4-difluorophenoxy)methanesulfonanilide; Fujisawa, Japan); FK 867 (Fujisawa, Japan); FR 115068 (Fujisawa, Japan); GR 253035 (Glaxo Wellcome); RWJ 63556 (Johnson & Johnson); RWJ 20485 (Johnson & Johnson); ZK 38997 (Schering); S 2474 ((E)-(5)-(3,5-di-tert-butyl-4-hydroxybenzylidene)-2-ethyl-1,2-isothiazolidine-1,1-dioxide indomethacin; Shionogi & Co., Ltd., Japan); CL 1004 (Parke-Davis); RS 57067 (Hoffmann La Roche); RS 104894 (Hoffmann La Roche); SC 41930 (Monsanto); SB 205312 (SmithKline Beecham); SKB 209670 (SmithKline Beecham, plc); and Ono 1078 (Ono Pharmaceutical Co., Japan).

3. Surface Stabilizers for Nanoparticles

The meloxicam particles of the present invention have at least one surface stabilizer adsorb on the surface thereof. Surface stabilizers useful herein physically adhere on or associate with the surface of the nanoparticulate meloxicam but do not chemically react with the meloxicam particles. The surface stabilizers are present in an amount sufficient to substantially prevent aggregation or agglomeration of the meloxicam particles during formation and/or administration of the meloxicam formulation.

Exemplary surface stabilizers include, but are not limited to, known organic and inorganic pharmaceutical excipients, as well as peptides and proteins. Such excipients include various polymers, low molecular weight oligomers, natural products, and surfactants. Useful surface stabilizers include nonionic surface stabilizers, anionic surface stabilizers, cationic surface stabilizers, and zwitterionic surface stabilizers. Combinations of more than one surface stabilizer can be used in the invention.

Representative examples of surface stabilizers include, but are not limited to, to foregoing alone or in combination: hydroxypropyl methylcellulose (HPMC); dioctyl sodium succinate (DOSS); sodium lauryl sulfate (SLS) a.k.a. sodium dodecyl sulfate (SDS); hydroxypropyl cellulose grade HPC-SL (viscosity of 2.0 to 2.9 mPa·s, aqueous 2% W/V solution, 20 DEG C., Nippon Soda Co., Ltd.); polyvinylpyrrolidone (PVP) such as Kollidone® K12 sold by BASF a.k.a. Plasdone® C-12 sold by ISP Technologies, Inc. (USA), Kollidone® K 7 sold by BASF a.k.a. Plasdone® C-17 sold by ISP Technologies, Inc. (USA), Kollidone®) K29/32 sold by BASF a.k.a. Plasdone® C-29/32 sold by ISP Technologies, Inc. (USA); sodium deoxycholate; block copolymers based on ethylene oxide and propylene oxide commonly known as poloxamers which are sold under the Pluronic® name by BASF (sold under the trade name Lutrol® in EU) and include Pluronic® F 68 a.k.a. poloxamer 188, Pluronic® F 108, a.k.a. poloxamer 338, Pluronic® F 127 a.k.a poloxamer 407; benzalkonium chloride a.k.a. alkyldimethylbenzylammonium chloride; copolymers of vinylpyrrolidone and vinyl acetate commonly known as copovidone sold under the tradename Plasdone® S-630 by ISP Technologies, Inc. (USA); lecithin; distearyl palmitate glyceryl; polyoxyethylene sorbitan fatty acid esters commonly known as polyoxyethylene 20 sorbitan monolaurate a.k.a. "polysorbate 20", polyoxyethylene 20 sorbitan monopalmitate a.k.a. "polysorbate 40," polyoxyethylene 20 sorbitan monooleate a.k.a. "polysorbate 80" sold under the trade names Tween® 20, Tween® 40 and Tween® 80, respectively, by ICI Americas; albumin; lysozyme; gelatin; macrogol 15 hydroxystearate sold as Solutol® 15 by BASF; tyloxapol, and polyethoxylated castor oils sold under the trade name Cremophor® EL by BASF.

Other surface stabilizers include, but are not limited to, hydroxypropylcellulose, random copolymers of vinyl pyrrolidone and vinyl acetate, casein, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000); polyethylene glycols (e.g., Carbowaxes 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminum silicate, triethanolamine, polyvinyl alcohol (PVA), 4-(1,1,3, 3-tetramethylbutyl)-phenol polymer with ethylene oxide and formaldehyde (also known as tyloxapol, superione, and triton); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.); Tetronic 1508® (T-1508) (BASF Wyandotte Corporation), Tritons X-200®, which is an alkyl aryl polyether sulfonate (Dow); Crodestas F-110, which is a mixture of sucrose stearate and sucrose distearate (Croda Inc.); p-isononylphenoxypoly-(glyc-idol), also known as Olin-10G® or Surfactant 10-G® (Olin Chemicals, Stamford, Conn.); Crodestas SL-40® (Croda, Inc.); and $SA_9OHCO$, which is $C_{18}H_{37}CH_2C(O)N(CH_3)$—$CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, and the like.

Additional examples of useful surface stabilizers include, but are not limited to, polymers, biopolymers, polysaccharides, cellulosics, alginates, phospholipids, poly-n-methyl-pyridinium chloride, anthryul pyridinium chloride, cationic phospholipids, chitosan, polylysine, polyvinylimidazole, polybrene, polymethylmethacrylate trimethylammonium bromide (PMMTMABr), hexyldecyltrimethylammonium bromide (HDMAB), and polyvinylpyrrolidone-2-dimethyl-aminoethyl methacrylate dimethyl sulfate.

Still further examples of useful stabilizers include, but are not limited to, cationic lipids, sulfonium, phosphonium, and quarternary ammonium compounds, stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)4 ammonium chloride or bromide, N-alkyl $(C_{12-18})$dimethylbenzyl ammonium chloride, N-alkyl $(C_{14-18})$dimethyl-benzyl ammonium chloride, N-tetradecylidmethylbenzyl ammonium chloride monohydrate, dimethyl didecyl ammonium chloride, N-alkyl and $(C_{12-14})$ dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl$(C_{12-14})$ dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (sold under the ALIQUAT 336 trade name of the Henkel Corporation), Polyquaternium-10, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Additional exemplary surface stabilizers are described in detail in the *Handbook of Pharmaceutical Excipients*, published jointly by the American Pharmaceutical Association and The Pharmaceutical Society of Great Britain, the Pharmaceutical Press, 2005. The surface stabilizers are commercially available and/or can be prepared by techniques known in the art. Presentations of exemplary surface stabilizers are given in McCutcheon, *Detergents and Emulsifiers*, Allied Publishing Co., New Jersey, 2004 and Van Os, Haak and Rupert, *Physico-chemical Properties of Selected Anionic, Cationic and Nonionic Surfactants*, Elsevier, Amsterdam, 1993; *Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990); all of which are incorporated by reference.

4. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients depending on the final dosage form of the commercial product. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of a powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, mint flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

5. Meloxicam Particle Size

In exemplary embodiments of the invention, compositions comprising meloxicam nanoparticles are defined by a particle size distribution. The particle size distribution is characterized by an effective average particle size. Nanoparticle meloxicam composition s of the invention have an effective particle size of less than about 2000 nm (i.e., 2 microns), less than about 1500 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

The distribution of medicament particles is also characterized by $D_{value}$. The nomenclature "D" followed by a number, e.g., $D_{50}$, is the particle size at which 50% of the particles in a particle size distribution are smaller and 50% of the particles are larger, when measured on a weight or volume basis. In another example, the $D_{90}$ of a particle size distribution is the particle size below which 90% of particles fall, and which conversely, only 10% of the particles are of a larger particle size, when measured on a weight or volume basis. The $D_{90}$ of the distribution of medicament particles according to an embodiment of the invention is 2000 nm (2 μm), 1900 nm, 1800 nm, 1700 nm, 1600 nm, 1500 nm, 1400 nm, 1300 nm, 1200 nm, 1100 nm, 1000 nm (1 μm), 900 nm, 800 nm, 700 nm, 600 nm, 500 nm, 400 nm, 300 nm, 200 nm, 150 nm, 100 nm, 75 nm, and 50 nm.

If the composition additionally comprises one or more non-meloxicam nanoparticulate active agents, then such active agents have an effective average particle size of less than about 2000 nm (i.e., 2 microns), less than about 1500 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

6. Concentration of Nanoparticulate Meloxicam, Surface Stabilizers, and Optional One or More Active Agents The concentration of meloxicam can vary from about 99.5% to about 0.001%, from about 95% to about 0.1%, and from about 90% to about 0.5%, by weight, based on the total combined weight of the meloxicam and at least one surface stabilizer, not including other excipients.

In a given unit dosage form, according to certain embodiments of the invention, the dosage form comprises range of 2.5 to 120 mg, such as 2.5, 5, 7.5, 15, 30, 60, 75, 90, 105, or 120 mg of meloxicam.

The concentration of the at least one surface stabilizer can vary from about 0.01% to about 99.5%, from about 0.1% to about 95%, and from about 0.5% to about 90%, by weight, based on the total combined dry weight of the meloxicam and at least one surface stabilizer, not including other excipients.

7. Methods of Making Nanoparticulate Formulations

The nanoparticulate meloxicam compositions can be made using, for example, milling, homogenization, or precipitation techniques. Exemplary methods of making nanoparticulate compositions are described in the '684 patent. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

One or more non-meloxicam active agents can also be reduced in size at the same time as meloxicam, to produce a nanoparticulate meloxican and nanoparticulate non-meloxicam active agent composition. A non-meloxicam active agent, which is either conventional or nanoparticulate sized, can also be added to the nanoparticulate meloxicam composition after size reduction.

In yet another embodiment of the invention, nanoparticulate meloxicam compositions of the invention can be made in which the formulation comprises multiple nanoparticulate meloxicam compositions, each of which has a different effective average particle size. Such a composition can be made by preparing the individual nanoparticulate meloxicam formulations using, for example, milling, precipitation, or homogenization techniques, followed by combining the different compositions to prepare a single dosage form.

B. Methods of Making Nanoparticulate Meloxicam Compositions

1. Milling to Obtain Nanoparticulate Meloxicam Dispersions

Milling meloxicam to obtain a nanoparticulate dispersion comprises dispersing meloxicam particles in a liquid dispersion medium in which meloxicam is poorly soluble, followed by applying mechanical means in the presence of rigid grinding media to reduce the particle size of meloxicam to the desired effective average particle size. The dispersion medium can be, for example, water, safflower oil, ethanol, t-butanol, glycerin, polyethylene glycol (PEG), hexane, or glycol.

The meloxicam particles can be reduced in size in the presence of at least one surface stabilizer. Alternatively, the meloxicam particles can be contacted with one or more surface stabilizers after attrition. Other compounds, such as a diluent, can be added to the meloxicam/surface stabilizer composition during the size reduction process. Dispersions can be manufactured continuously or in a batch mode. The resultant nanoparticulate meloxicam dispersion can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

2. Precipitation to Obtain Nanoparticulate Meloxicam Compositions

Another method of forming the desired nanoparticulate meloxicam composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving meloxicam in a suitable solvent; (2) adding the formulation from step (1) to a solution comprising at least one surface stabilizer, and (3) precipitating the formulation from step (2) using an appropriate non-solvent. The method can be followed by removal of any formed salt, if present, by dialysis or diafiltration and concentration of the dispersion by conventional means. The resultant nanoparticulate meloxicam dispersion can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

3. Homogenization to Obtain Meloxicam Nanoparticulate Compositions

Exemplary homogenization methods of preparing active agent nanoparticulate compositions are described in U.S. Pat. No. 5,510,118, for "Process of Preparing Therapeutic Compositions Containing Nanoparticles." Such a method comprises dispersing meloxicam particles in a liquid dispersion medium, followed by subjecting the dispersion to homogenization to reduce the particle size of the meloxicam to the desired effective average particle size. The meloxicam particles can be reduced in size in the presence of at least one surface stabilizer. Alternatively, the meloxicam particles can be contacted with one or more surface stabilizers either before or after attrition. Other compounds, such as a diluent, can be added to the meloxicam/surface stabilizer composition either before, during, or after the size reduction process. Dispersions can be manufactured continuously or in a batch mode. The resultant nanoparticulate meloxicam dispersion can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

C. Methods of Using Meloxicam Formulations of the Current Invention

The meloxicam compositions of the present invention can be administered to a subject via any conventional means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably.

The present invention provides a method of rapidly increasing the plasma levels of orally administered meloxicam in a subject. Such a method comprises administering to a subject an effective amount of an orally administered composition comprising nanoparticulate meloxicam.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, softgels, gummies, and elixirs. In addition to the active agent, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Ocular dosage forms of the nanoparticulate meloxicam of the invention preferably do not include cross-linked carboxyl-containing polymers, used as excipients, as described in U.S. Pat. No. 5,192,535. Such excipients can be undesirable.

EXAMPLES

The following examples are given to illustrate the present invention. It should be understood, however, that the invention is not to be limited to the specific conditions or details described in these examples.

Example 1

This example identifies and exemplary method to prepare a nanoparticulate meloxicam dispersion suitable for injection.

A slurry of 20% (w/w) meloxicam and 4% (w/w) polyvinyl pyrrolidone were milled in a NanoMill) milling system (Elan Drug Delivery, Inc., King of Prussia, Pa.; see e.g., U.S. Pat. No. 6,431,478 for "Small Scale Mill").

Example 2

Aqueous dispersions of 5 wt. % meloxicam and 1 wt. % stabilizer (see Table 1, below) were charged into a NanoMill® milling system (Elan Drug Delivery, Inc., King of Prussia, Pa.; see e.g., U.S. Pat. No. 6,431,478 for "Small Scale Mill").

Particle size analysis of the resultant milled dispersions was performed using a Horiba LA-910 particle size analyzer (Horiba Instruments, Irvine, Calif.). The results are shown below in Table 1. In the table below, the value for D50 is the particle size below which 50% of the active agent particles fall. Similarly, D90 is the particle size below which 90% of the active agent particles fall.

TABLE 1

| Stabilizer | Mean (nm) | D50 (nm) | D90 (nm) | Optical Microscopy* |
|---|---|---|---|---|
| poloxamer 188 | 133 | 110 | 226 | Stable |
| poloxamer 388 | 129 | 108 | 219 | Stable |
| polyvinylpyrrolidone k-12 | 98 | 90 | 125 | Stable |
| polyvinylpyrrolidone k-17 | 98 | 95 | 135 | Stable |
| Polysorbate 80 | 227 | 227 | 322 | Stable |
| Sodium Deoxycholate | 119 | 101 | 198 | Stable |
| Lecithin | 190 | 169 | 271 | Mild aggregation at initial |
| Lysozyme | 95 | 89 | 117 | Moderate aggregation at initial; Stable at 24 hours |

All formulations were taken at initial time except for Lecithin and Lysozyme. For those samples, the "initial particle size" was measured at 24 hr post milling.

The results demonstrate that meloxicam can be formulated into stable nanoparticulate compositions suitable for IV administration with each of the surface stabilizers shown in Table 1, as all of the formulations have a particle size suitable for injectable compositions. Nanoparticulate compositions shown in Table 1 had mean particles sizes ranging from 95 to 227 nm, with D50 and D90 sizes ranging from 89 nm to 227 nm and 117 nm to 322 nm, respectively.

Example 3

The purpose of this example was to test the stability of a nanoparticulate meloxicam formulation comprising mannitol.

A slurry of 10% (w/w) meloxicam, 2.5% (w/w) polyvinylpyrrolidone, 0.75% (w/w) NaDOC and 10% (w/w) mannitol was milled to obtain a nanopartiuclate dispersion of meloxicam. The nanoparticulate meloxicam dispersion was diluted to 5% meloxicam, 1.25% polyvinylpyrrolidone, 0.375% NaDOC, 5% mannitol and 15% sucrose with a 30% sucrose solution. The formulation was stored at 5° C. for 3 months. The resulting nanoparticulate meloxicam formulation did not show any significant particle agglomeration or aggregation.

Example 4

The purpose of this example was to test in vivo the meloxicam compositions.

Four male and four female Beagle dogs were fasted overnight. In addition, each dog was fasted for four (4) hours post dose. Each dog received three different meloxicam formulations, which are described in more detail below. Formulation #1 was a liquid dispersion of nanoparticulate meloxicam particles; Formulation #2 was a lyophilized table of nanoparticulate meloxicam particles; and Formulation #3 was a MOBIC® 7.5 mg tablet (Boehringer Ingelheim Pharmaceuticals, Inc.).

Formulation #1 (liquid dispersion): 8.0 g meloxicam was milled with a solution containing 1.6 g Poloxamer 407 and 70.4 g water. The mean (weight average) final meloxicam particle size was 111 nm, as measured on a Horiba LB-910 particle size analyzer (Horiba Instruments, Irvine, Calif.). 5 grams of the meloxicam dispersion was then added to 45 grams of water to give a final concentration of 1% meloxicam.

Formulation #2 (lyophilzed wafers): A "fast melt" lyophilized dosage form was prepared from a nanoparticulate dispersion of meloxicam to study the relationship between the lyophilization and reconstitution process and the pharmacokinetic data. 8.0 g meloxicam was added to a solution containing 2.4 g polyvinylpyrrolidone, 1.6 g docusate sodium, and 68 g water. The mean particle size of the meloxicam dispersion following milling was 101 nm, as measured on a Horiba LA-910 particle size analyzer. Mannitol, pullulan and glycerol were added to the dispersion and placed in a lyophilizer to produce the final lyophilized wafer dosage form. After 2.5 months the reconstituted mean particle size of the meloxicam particles was 111 nm.

Formulation #3 (tablet): MOBIC® Tablets (Boehringer Ingelheim), 7.5 mg.

Dog Study Protocol

In Phase 1, each dog received a single oral gavage dose of 7.5 mg meloxicam (Formulation #1), followed by an approximately 10 mL tap water flush of the gavage tube.

In Phase 2, after a 7-day washout period, the same eight dogs received a 7.5 mg dose of meloxicam as a single lyophilized wafer (Formulation #2).

In Phase 3, after a 7-day washout period, the same 8 dogs received a single 7.5 mg tablet of MOBIC® (lot #251586N) (Formulation #3).

Results

Blood samples were collected and processed to plasma at the conclusion of each phase as follows: Blood samples (approximately 1 mL) were drawn at specified time points (blood collected predose and at 0.167, 0.333, 0.5, 0.75, 1, 1.5, 2, 2.5, 3, 4, 6, 8, 12, 16, 24, and 48 hours postdose). The Cmax, Tmax, and AUC for the three different formulations are shown below in Table 2.

TABLE 2

| Formulation | Cmax (μg/mL) | Tmax (hours) | AUC |
|---|---|---|---|
| 1 (liquid dispersion) | 3.499 | 0.750 | 118.225 |
| 2 (lyophilized wafer) | 3.420 | 1.292 | 106.642 |
| 3 (MOBIC ®) | 2.768 | 3.375 | 99.870 |

Both the liquid dispersion of nanoparticulate meloxicam (Formulation #1) and the lyophilized wafer of nanoparticulate meloxicam (Formulation #2) showed a faster onset time and a larger Cmax than the commercial MOBIC® tablet. In addition, the smaller particle sizes of the nanoparticulate meloxicam formulations resulted in faster dissolution, thereby producing a much shorter Tmax (0.75 and 1.3 hours, respectively, for Formulations #1 and #2, as compared to 3.4 hours for Formulation #3). See FIG. 1.

Example 5

The formulation of Example 3 was evaluated in a single-dose, crossover study following intravenous administration to humans. The safety, tolerability, and pharmacokinetics were compared to commercially available oral meloxicam tablets, 7.5 mg and 15 mg MOBIC® tablets, NDA 020938 approval date 13 Apr. 2000 (Boehringer Ingelheim).

As reported on the 27 Jun. 2008 label for MOBIC® tablets, meloxicam oral suspension doses of 7.5 mg/5 mL and 15 mg/10 mL have been found to be bioequivalent to meloxicam 7.5 mg and 15 mg capsules, respectively. Meloxicam capsules have been shown to be bioequivalent to Mobic® (meloxicam) tablets. See table 1 of the MOBIC® tablet label reproduced below.

TABLE 3

Single Dose and Steady State Pharmacokinetic Parameters for Oral 7.5 mg and 15 mg Meloxicam (Mean and % CV)[1]

| | | Steady State | | | |
|---|---|---|---|---|---|
| | Healthy | | | Single Dose | |
| Pharmacokinetic Parameters (% CV) | male adults (Fed)[2] 7.5 mg[3] tablets | Elderly males (Fed)[2] 15 mg capsules | Elderly females (Fed)[2] 15 mg capsules | Renal failure (Fasted) 15 mg capsules | Hepatic insufficiency (Fasted) 15 mg capsules |
| N | 18 | 5 | 8 | 12 | 12 |
| $C_{max}$ [μg/mL] | 1.05 (20) | 2.3 (59) | 3.2 (24) | 0.59 (36) | 0.84 (29) |
| $t_{max}$ [h] | 4.9 (8) | 5 (12) | 6 (27) | 4 (65) | 10 (87) |
| $t_{1/2}$ [h] | 20.1 (29) | 21 (34) | 24 (34) | 18 (46) | 16 (29) |
| CL/f [mL/min] | 8.8 (29) | 9.9 (76) | 5.1 (22) | 19 (43) | 11 (44) |
| $V_z/f^4$ [L] | 14.7 (32) | 15 (42) | 10 (30) | 26 (44) | 14 (29) |

[1]The parameter values in the Table are from various studies
[2]not under high fat conditions
[3]MOBIC tablets
[4]$V_Z/f = Dose/(AUC \cdot K_{el})$ A single-dose, randomized, 2-treatment, 3-cohort (n=7), open label crossover study of 3 dose levels (15 mg, 30 mg, and 60 mg) of meloxicam of the present invention administered intravenously and commercially available meloxicam (MOBIC® tablets) administered orally was conducted. An exemplary method of administrating an embodiment of the present invention is intravenous (IV) injection, such as, but not limited to, slow intravenous (IV) push over 2 minutes or less.

Cohort 1 received 15 mg, cohort 2 received 30 mg, and cohort 3 received 60 mg of meloxicam according to the present invention. Blood plasma drug concentrations and safety evaluations were obtained at various times following dosing, up to 72 hours postdose.

The following table displays the mean pharmacokinetic parameters of an exemplary meloxicam composition following a single dose exposure in healthy volunteers and the commercially available meloxicam MOBIC® tablet for each cohort. Within each cohort, the elimination rate and half life of the meloxicam were similar and expected. Table 4 is a summary of pharmacokinetic parameters of mean $AUC_{last}$ and mean $AUC_{inf}$ for cohort 1, 2, and 3.

TABLE 4

| Dosage Amount of Meloxicam (mg) | AUC (ng * hr/mL) | Statistic | Exemplary embodiment of the present invention | MOBIC ® Tablet |
| --- | --- | --- | --- | --- |
| Cohort 1: 15 | last | Mean (SD) | 46094.8 (14565.8) | 42949.2 (11662.8) |
| | inf. | Mean (SD) | 57314.4 (27233.2) | 53988.8 (23207.7) |
| Cohort 2: 30 | last | Mean (SD) | 92575.9 (18456.0) | 88340.6 (16547.1) |
| | inf. | Mean (SD) | 107508.7 (34443.0) | 104400.0 (30656.2) |
| Cohort 3: 60 | last | Mean (SD) | 156042.6 (24041.4) | 146677.3 (21925.3) |
| | inf. | Mean (SD) | 171229.0 (34439.1) | 163854.7 (32916.7) |

Example 6

The purpose of this example was to evaluate the analgesic efficacy of a single intravenous (IV) dose of the meloxicam formulations made in accordance with Example 3 with varying dose amount (15 mg, 30 mg, and 60 mg).

A randomized, single-dose study was completed in a post dental surgical setting. The study was conducted on subjects who underwent surgical removal of at least two, third molars with at least one mandibular impaction. Following dental surgery, subjects were randomly assigned treatment: placebo, 15 mg meloxicam IV, 30 mg meloxicam IV, 60 mg meloxicam IV, or MOTRIN® IB (ibuprofen) 400 mg. MOTRIN® IB was given as 2, 200 mg tablets orally (400 mg total). Subjects were dosed within 5 hours and only when their pain intensity (PI) rating was moderate to severe on a 4-point Likert Scale (with categories of none, mild, moderate, or severe). Efficacy measurements were made regularly up to a 24 hour time period.

Pain intensity (PI) and pain relief (PR) were recorded at 10, 20, 30, and 45 mins, 1, 1.5, 2, 3, 4, 5, 6, 8, 20, 12, 18, and 24 hours after dosing. Time of onset was determined using a two-stopwatch technique. Stopwatches were started when the subjects received their study medication. Subjects were instructed to stop the first stopwatch when pain relief was initially perceptible (PI), and stop the second stopwatch when pain relief was considered meaningful (PR). The duration of analgesia is represented by the time interval between administration of the study drug and administration of the rescue drug, if requested. If no rescue drug was requested, pain relief was recorded for up to 24 hours post administration.

Figure 3:
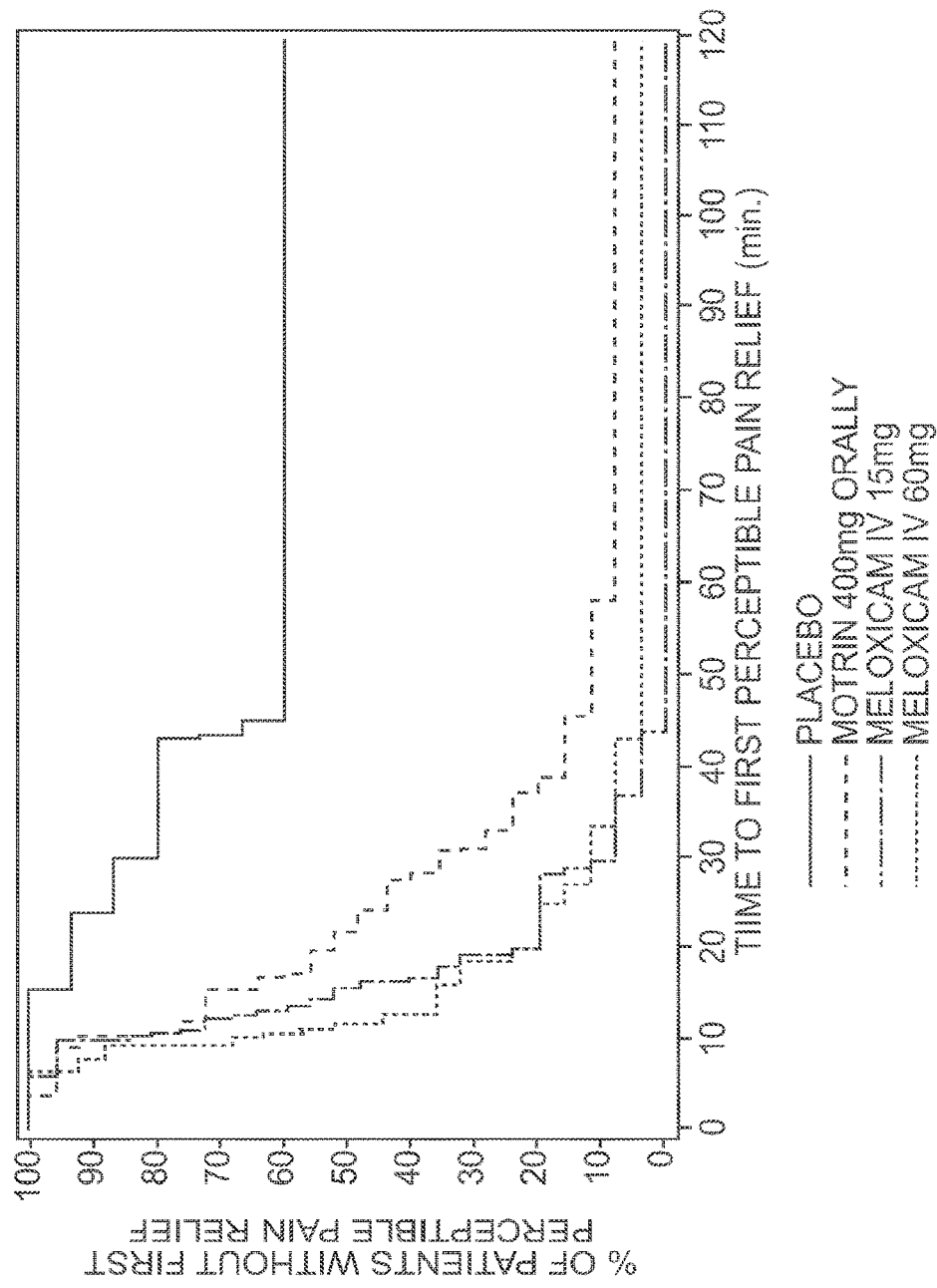
FIG. 3 is a plot of the percentage of patients without first perceptible pain relief over time to first perceptible pain relief.

FIG. 3 is a plot of the percentage of patients without first perceptible pain relief over time to first perceptible pain relief for those patients who were given the placebo, MOTRIN) IB (ibuprofen) 400 mg, 15 mg meloxicam IV, or 60 mg meloxicam IV. After 20 minutes, greater than 80% of the patients given either the 15 mg meloxicam IV or 60 mg meloxicam IV reported first perceptible pain relief.

Figure 4:
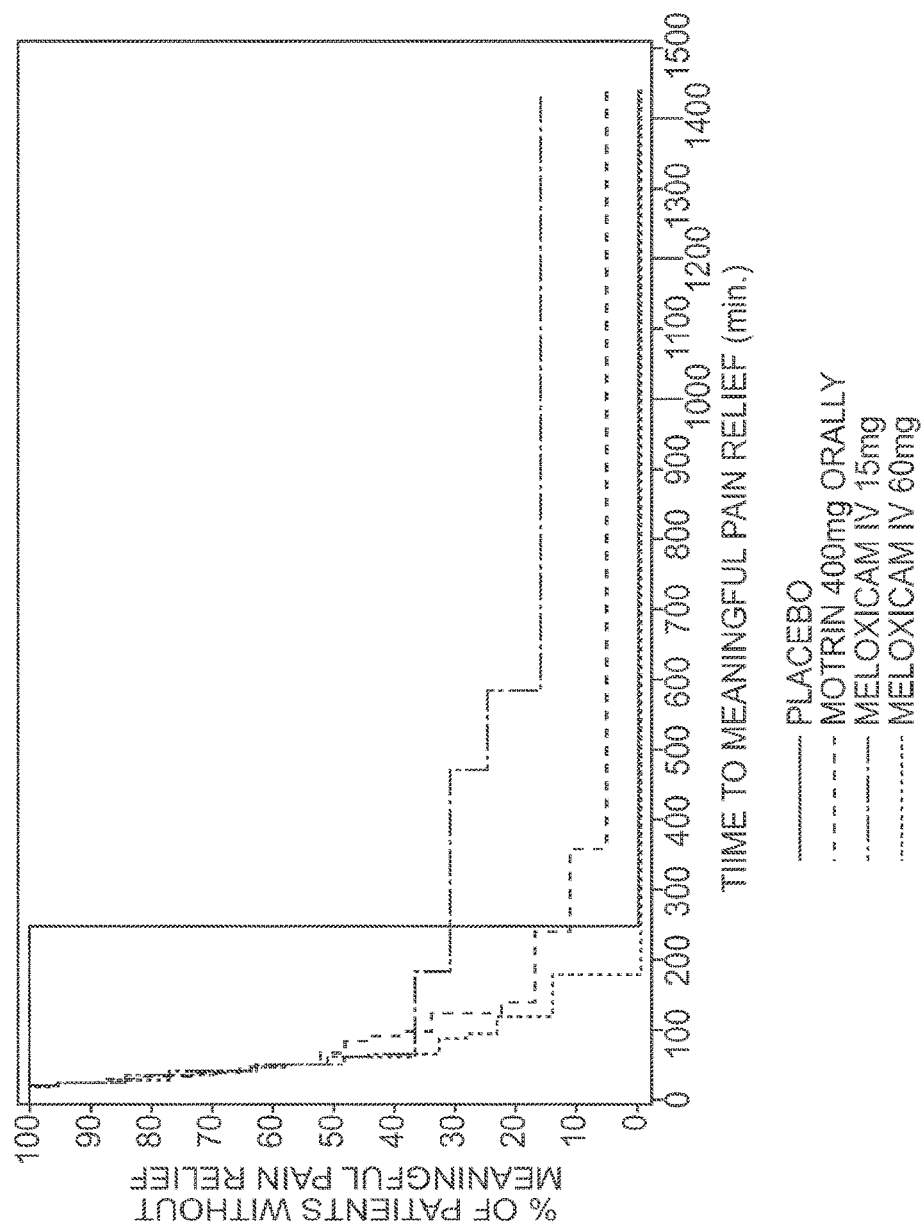
FIG. 4 is a plot of the percentage of patients without meaningful pain relief over time to meaningful pain relief.

FIG. 4 is a plot of the percentage of patients without meaningful pain relief over time to meaningful pain relief for those patients who were given the placebo, MOTRIN® IB (ibuprofen) 400 mg, 15 mg meloxicam IV, or 60 mg meloxicam IV. After 2 hrs, greater than 60% of the patients given either the 15 mg meloxicam IV or 60 mg meloxicam IV reported meaningful pain relief.

Figure 5:
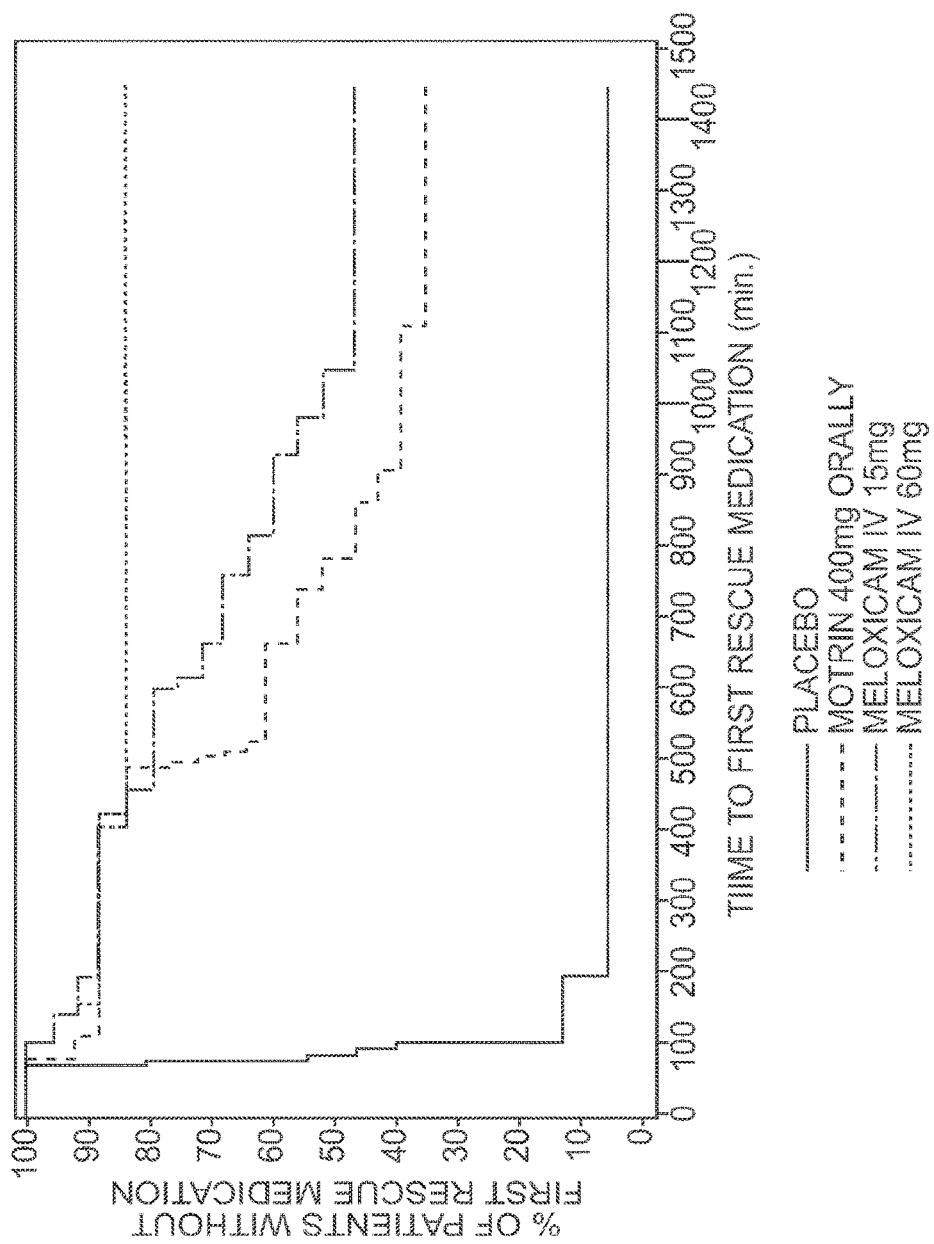
FIG. 5 is a plot of the percentage of patients without rescue medication over time.

FIG. 5 is a plot of the percentage of patients without first rescue medication over time to when the patient received the rescue medication for those patients who were given the placebo, MOTRIN® IB (ibuprofen) 400 mg, 15 mg meloxicam IV, or 60 mg meloxicam IV. More than 80% of patients given the 60 mg meloxicam IV did not request rescue medication for up to 24 hours (1440 min.). Also more than 40% of patients given the 15 mg meloxicam IV did not request rescue medication for up to 24 hours (1440 min.). In other words, patients who received either the 15 mg meloxicam IV or 60 mg meloxicam IV experienced efficacious pain relief for up to 24 hours.

What is claimed:

1. An injectable pharmaceutical dosage form consisting of:
   30 mg of meloxicam, or a salt thereof, wherein the meloxicam is in the form of particles having an effective average particle size of less than about 200 nm;
   polyvinylpyrrolidone;
   sodium deoxycholate;
   sucrose; and
   water.

2. The dosage form of claim 1, wherein the effective average particle size of the meloxicam particles, or a salt thereof, is less than about 150 nm.

3. The dosage form of claim 1, wherein the effective average particle size of the meloxicam particles, or a salt thereof, is less than about 100 nm.

4. A method of administering meloxicam to a human in need thereof comprising intravenously or intramuscularly injecting the pharmaceutical dosage form of claim 1 into the human.

* * * * *